United States Patent [19]
Franson et al.

[11] Patent Number: 5,659,055
[45] Date of Patent: Aug. 19, 1997

[54] CYTOPROTECTIVE FATTY MOIETY COMPOUNDS

[75] Inventors: Richard C. Franson, Richmond; Raphael M. Ottenbrite, Midlothian, both of Va.

[73] Assignee: Virginia Commonwealth University, Richmond, Va.

[21] Appl. No.: 475,335

[22] Filed: Jun. 7, 1995

Related U.S. Application Data

[63] Continuation of Ser. No. 10,456, Jan. 27, 1993, abandoned, which is a continuation-in-part of Ser. No. 399,941, Aug. 29, 1989, which is a continuation-in-part of Ser. No. 256,330, Oct. 11, 1988, which is a continuation-in-part of Ser. No. 156,739, filed as PCT/US87/00408, Feb. 24, 1987.

[51] Int. Cl.$^6$ ............................................. C07B 45/00
[52] U.S. Cl. ......................... 554/88; 554/94; 554/103; 554/108; 554/110; 554/223; 554/224; 554/227
[58] Field of Search ........................ 554/88, 94, 110, 554/223, 224, 227, 103, 108

[56] References Cited

U.S. PATENT DOCUMENTS 4,701,469  10/1987  Mendy et al. ........................ 514/547

OTHER PUBLICATIONS

Chemical Abstracts, 103:183451, O'Brien et al., abstract of article including compound, "Preparation and characterization od polymerized liposomes". 1985.

*Primary Examiner*—Deborah D. Carr
*Attorney, Agent, or Firm*—Jones & Askew

[57] ABSTRACT

Water or lipid soluble, pharmacologically active, antioxidant, anti-phospholipase compounds that are chemically defined. The compounds protect mammalian cells by inhibiting $PLA_2$ and preventing oxidation. In particular, each compound has at least two fatty moieties and no active hydroxy group. The compound may also have at least one ionizable group, which may be a carboxyl group, and each of the fatty moieties has from sixteen to twenty carbon atoms and at least one cis-unsaturated double bond.

5 Claims, 7 Drawing Sheets

CYTOPROTECTIVE FATTY MOIETY COMPOUNDS

CROSS-REFERENCES TO RELATED APPLICATIONS

This application is a continuation of application Ser. No. 08/010,456, filed Jan. 27, 1993, now abandoned, which is a continuation-in-part of prior co-pending application Ser. No. 07/399,941 filed Aug. 29, 1989, which in turn is a continuation-in-part of prior co-pending application Ser. No. 07/256,330 filed Oct. 11, 1988, which again in turn is a continuation-in-part of prior co-pending applications Ser. No. 07/156,739 filed Feb. 18, 1988 and Ser. No. PCT/US87/00408 filed Feb. 24, 1987. This application and the identified prior applications are all assigned to the common assignee, Virginia Commonwealth University, and the subject matter of each prior application is hereby specifically incorporated herein by reference.

BACKGROUND OF THE INVENTION

1. Field of the Invention

The present invention relates to methods and materials for protecting mammalian cells from injury due to intrinsic membrane lysis, oxidation and/or invasion by destructive agents. In particular the invention relates to materials and methods for treating against and/or prophylactically inhibiting the injury causation. Even more particularly, the invention relates to bioactive agents and the use thereof for treating or prophylactically inhibiting phospholipase mediated injury and/or injury due to oxidation. In a specific sense the invention provides agents for preventing and/or treating inflammation and cell destruction in mammalian tissue and for protection and preservation of biologic material such as food and tissue samples.

2. The Prior Art Environment

The base structure of all living organisms is the cell which is structurally defined by its membranous lipoprotein envelope. The membranous network that holds the cell together maintains the ionic balance and provides the receptors to hormones and neurotransmitters that enable a cell to interact with its environment. This is pertinent to interaction with neighboring cells which enable isolated cells, tissues, or whole organisms to survive as both independent units and as participants in cellular interactions, in vitro and in vivo. Nutritional, kinetic electro-physiological, excretory, and reproductive mechanisms are mediated through the self renewal of the lipoprotein membranes that bind the cell, its nucleus and organelles into a functional whole.

The cell has a preordained life to live in accordance with the balance superimposed by the information provided by the nucleus and the environment. A cell has a date of conception and a circumstance mediated or preordained time to die. The dictates of certain circumstances, i.e., physiological stimuli or pathologic injury, prescribe the manner of death and the time of death of cells. Cell death and/or injury is the result of both intrinsic and extrinsic factors and is key to the fate of the larger organism of which cells are a critical and necessary part.

That which is good for the cell, that which maintains its capacity to respond to change to ionic fluxes that maintain membrane potential and to repair injury under normal conditions should be good for its host or supportive to in vitro biologic production (i.e., tissue culture, monoclonal antibody, enzyme or endocrine production of pertinence to biotechnology). The integrity of cell membranes which maintain ionic flux, and electro-physiologic and/or hormonal or messenger responses is the key to cellular functional survival and longevity. Repair and resistance to injury is a function of the maintenance of lipoprotein membrane integrity.

Factors which govern cell function, renewal, reproduction and death are controlled by their effects on the phospholipid/protein envelope or cytoskeleton. The cell membrane controls the cellular clocks and ionic fluxes which govern responsiveness and survival. Damage to phospholipid/proteins, with particular emphasis on lipid peroxidation, membrane oxidation and the action of phospholipases, governs resistance to injury, repair and host responses to environmental change and ionic and osmotic integrity.

Pathological events in a host under clinical circumstances result in massive cellular insult, initiated or mediated by loss of membrane integrity. The events are mediated by "death triggers" which digest and destroy cell membrane and propagate an injury by producing a cascade of cell membrane changes. Similar events in tissue culture are vital to the biologic availability of cells and cell products while still permitting cells to possess the capacity to respond to their environments or each other. By interfering with the cascade of external and internal events involving membrane integrity and toxic changes which lead to cell death, injury can be prevented, modified or reversed. This has been a major role of anti-inflammatory agents in the past.

The most important presently used clinically effective anti-inflammatory drugs include the corticosteroids and the non-steroidal anti-inflammatory agents (NSAIAs). These drugs act to control inflammation and to minimize cell injury by regulating the breakdown of phospholipids or the action of the products of such breakdown leading to the formation of prostaglandins and leukotrienes which are produced in increased quantities in inflammation and promote cell dysfunction and injury.

In addition, recent studies have demonstrated that cellular and extra cellular phospholipases may be activated by the generation of oxygen free radicals. This can establish a "vicious cycle" as phospholipase activation can release free radicals which, in turn, activate more phospholipases. In this regard, free radicals are produced from fatty acids released by the action of phospholipases, which are converted to prostaglandins and leukotrienes. Fatty acids and free radicals are known to be prime mediators in the cascade of reactions that result in membrane injury, cell death and inflammation.

In addition to effects involving free radical formation, an additional role for phospholipases, particularly phospholipase $A_2$ ($PLA_2$), is that through their action promoting fatty acid release, as an example they produce arachidonic acid derivatives that promote potassium ($K^+$) ion channel opening which governs the electrophysiologic and second messenger responses of the cell. Thus, phospholipase inhibitors can modulate cell responses to membrane stimulation governing cell function.

One of the hallmarks of inflammation and cell injury is the breakdown of cellular membrane phospholipid. Phospholipids are the major structural building blocks of the cell membrane; they give rise to the barrier-structural and functional properties of membranes and their integrity is crucial to normal cell responsiveness and function. Phospholipid changes in cell membrane integrity, particularly changes in fatty acids at the 2 position, alter the fluidity of cell membranes, their receptor availability and the leakiness or availability of cellular contents to the external environment.

The breakdown of phospholipid membranes results in "unraveling" or lysis of cells, or results in holes in the cell membrane, the disruption or enhancement of ion channels, or the loss of membrane bound receptors which destroys integrity and functional survival.

During inflammation, phospholipases, from whatever source, that are normally under the control of natural suppressor systems, are activated to degrade membrane phospholipid which, in turn, generates oxygen free radicals. A key enzyme Which is activated in inflammation is phospholipase $A_2$ ($PLA_2$) which acts on phospholipids as enzyme targets to release free fatty acids. These fatty acids (i.e., arachidonate) released by $PLA_2$ are converted to potent biologically active metabolites, prostaglandins and leukotrienes, with the concomitant generation of oxygen free radicals. These $PLA_2$ products have effects on K ion channels and G proteins involved in second messenger cell responses involved in cell membrane homeostasis. These metabolites, fatty acids and free radicals, are powerful mediators of pathophysiology Which propagate injury and cell death or permit the nidation, survival and growth of pathogens or tumor cells.

The role of phospholipases, particularly $PLA_2$, as membrane targeted enzymes, make them veritable "death triggers" as the expression of their degradation activity results in further production of inflammatory mediators leading to further membrane injury which propagates damage within the cell itself or into adjacent tissue. Thus, the spread of injury from the initial site to contiguous or distant sites can be promoted by the activation and/or release of $PLA_2$.

In addition to the intrinsic membrane-related tissue breakdown via the activation of $PLA_2$, phospholipases, and particularly $PLA_2$, are part of the normal defensive system of the body. $PLA_2$ is found in particularly high levels in human white blood cells (WBCs): polymorphonuclear leukocytes (PMNs) and phagocytic cells. WBCs play a role in resisting infection, but when these cells are mobilized to ward off injury and infection, $PLA_2$ is released from adherent and circulating WBCs and produces local tissue necrosis which increases the extent of initial injury. In addition, WBCs adhere to blood vessel walls where they release enzymes such as $PLA_2$. WBCs also generate free radicals and thus promote damage to the vascular endothelium, lung alveoli or to tissue sites contiguous with WBC infiltration or concentration. Where inflammation is found, WBCs are usually present in abundance and the WBCs adhere to vascular endothelium, with release and activation of $PLA_2$ resulting in damage to vascular integrity during shock and ischemia. Thus, in spite of being a prime defensive system of the body against infection, WBCs can also damage the body by propagating injury and inflammation beyond their normal defensive role.

The classic description of inflammation is "redness and swelling with heat and pain (Celsus, 100 AD)." Inflammation has been defined as the reaction of irritated and damaged tissues which still retain vitality. Inflammation is a process which, at one level, can go on to cell death, tissue necrosis and scarring and at another level, inflammation can be resolved with a return to normalcy and no apparent injury or with minimal changes, i.e., pigmentation, fibrosis or tissue thickening with collagen formation related to healing and scarring. The process is dynamic, with cell death as one consequence, and recovery, healing and scarring as another. For inflammation to occur as a process, cells must retain their vitality. Dead or severely compromised cells do not respond to inflammatory reactions. Injury in inflammation can also relate to the late results of fibrosis and scarring with the loss of blood vessels, tissue elasticity and cosmetic quality.

Inflammation, while a normal process of the body's resistance to injury and infection, can become aberrant leading to propagated injury with extensive scarring, tissue death and/or the death of the organism. Within certain limits, the inflammatory reaction is stereotyped and it cannot distinguish between those instances in which the process protects the host and those in which the host is harmed.

Microscopically, inflammation is characterized by vasodilation, vascular leakage, enhanced lymphatic flow, platelet vascular adherence and clumping and WBC infiltration and vascular adherence and phagocytosis with slowing of blood flow, red cell aggregation resulting in the formation of blood clots. Clinically, these local phenomena can be associated with pain, fever and swelling which can lead to local tissue destruction (granulation, caseation and necrosis) healing or scarring or to systemic symptoms of pain, fever, shock (prostration) hypotension, leading to death or recovery.

Microscopically, inflammation has been described as related to: (1) atony of the muscle coat of the blood vessel wall; (2) increased resistance to blood flow related to friction and adhesiveness of blood elements (i.e., red blood cells, proteins, white blood cells, platelets); and (3) enhanced permeability, i.e., loss of red blood cells, white blood cells and blood fluid through the vascular wall.

In physiological terms, these are described as hyperemia, edema, blood stasis, thrombosis, and hemorrhage. Inflammation can be mediated by humoral substances produced by tissue elements or infectious agents or by changes in pH (acidity) or oxygen concentration. Clinically, pain, fever, malaise, muscle, arterial and visceral spasm as well as headache and confusion states can accompany inflammation for whatever primary cause.

The above events are often mediated by phospholipase activation, followed by fatty acid release and the formation of free radicals. These events can be endogenous to the matrix of the body, the supporting cells and tissues that are functionally or systemically integrated or related to specialized host defense mediating cells, i.e., induced by white blood cells or platelet activity which respond as part of the body's defenses and which release phospholipases or free radicals as part of their role in resistance to infection, or their place in the normal maintenance of coagulative or vascular integrity, i.e., the prevention of hemorrhage, thrombosis or ischemia.

Alternatively, phospholipase activity can relate to exogenous enzyme activity released from infecting pathologic organisms such as viruses, bacteria, Rickettsia, protozoa, or fungi which posses phospholipase as factors intrinsic to their infectious activity. In this regard, infecting organisms such as bacteria, viruses, Rickettsia, protozoa or their toxins can stimulate infected cells or the endogenous defense system to release phospholipases, i.e., $PLA_2$, which can act locally or at distance sites to produce inflammation or tissue damage. In the case of Naegleria, a pathogenic amoeba with affinity for the brain, destruction of brain membranes induced by phospholipases secreted by Naegleria can occur at sites in the brain distant from where the organism is localized.

In regard to intrinsic effects of $PLA_2$, the same is produced in extremely high concentration by inflamed collagenous spinal discs where its localized action is associated with severe pain and muscle spasm, as part of low back and cervical cord injury resulting in acute or chronic discomfort.

Phospholipases released from infecting organisms or as a result of tissue injury can induce coagulation of blood proteins, producing ischemic injury at sites contiguous or distant to the primary disease. In considering the action of phospholipases, it must be recognized that their pathologic effects can be both local, regional or systemic. This is governed by the phospholipase enzyme released, the level of albumin, natural inhibitors of enzyme action, and factors of diffusion, circulation and tissue vulnerability based on intrinsic inhibitors or the susceptibility of previously damaged or oxidized membranes or proteins to phospholipase action.

Inflammation is associated with trauma, infection and host defense reactions, i.e., fever, malaise and shock, related to direct bacterial or virus killing or associated immune responses. Immune responses can be both beneficial, protective or tissue damaging as can be seen in their being responsible for resistance or cure of infection, or on the other hand, capable of producing autoimmune phenomenon that results in allergy, i.e., asthma, urticaria, host versus graft disease, glomerular nephritis, rheumatic fever, lupus and rheumatoid arthritis.

In regard to the current treatment of inflammation, corticosteroids are effective anti-inflammatories, but must be used with caution clinically because they are powerful immunosuppressants and inhibitors of fibroblast activity necessary for wound and bone repair. In addition, corticosteroids are diabetogenic drugs and their toxic side effects involve interference with wound repair and bone matrix formation, and result in sodium retention, potassium loss and decreased resistance to infection. Corticosteroids also have effects on steroid formation, blood pressure, protein utilization, fat distribution, hair growth and body habitus. Alternatively, the clinically active NSAIAs, such as aspirin, indomethacin, ibuprofen, etc., work by inhibiting the conversion of free fatty acids to prostaglandins. The side effects of NSAIAs include gastric ulceration, kidney dysfunction and Reye's Syndrome, and metabolites of prostaglandin can be either damaging or protective to cells depending on the structure of the prostaglandin produced or utilized pharmacologically and the route of administration, cell or tissue effected. In addition to effects on inhibition of cyclooxygenase, some of the NSAIAs, including ibuprofen, indomethacin and meclofenamate, directly inhibit $PLA_2$ activity in vitro.

As discussed previously, in conjunction with fatty acid release, as part of phospholipid cell membrane mediated injury produced by phospholipase activation, leukotrienes are generated. These leukotrienes produced from membrane phospholipid breakdown, damage tissue through direct toxic action, effects on ionic channels, and associated free radical formation; or by indirect effects on vascular smooth muscle or vascular endothelial lining via platelet, WBC, endothelial (blood vessel lining) or smooth muscle constricting interactions.

Leukotrienes are responsible for smooth muscle constriction leading to bronchospasm and the asthmatic attacks seen in allergy or infectious asthma. Thus, there is an ongoing active search for leukotriene inhibitors for clinical application in the treatment of allergy, asthma and tissue injury and inflammation.

Because the phospholipase activated biochemical pathway for the formation of prostaglandins and leukotrienes derived from free fatty acids is branched, inhibition of one branch of this pathway, as with NSAIAs, can create an imbalance in these reactive metabolites. This imbalance may actually aggravate inflammation and promote cell injury as evidenced by the gastric ulceration side effects of NSAIA's, which, along with pH changes have intraperitoneal inflammatory effects.

Due to these adverse effects of both steroids and NSAIAs, there is currently much clinical medical interest in identifying phospholipase inhibiting agents that do not have steroidal side effects, but like corticosteroids modulate the first step leading to the production of injurious metabolites, fatty acids and free radicals.

Free radicals, produced by white blood cells, tissue injury or metabolic processes, are highly reactive chemical species which, in the case of tissue injury, are most often derived from respiratory oxygen. Oxygen, while necessary for energetics of life, is also a toxin which, as the chemically related superoxide, or as peroxides, can damage tissue instead of supporting it. Free radicals derived from oxygen are critical to damage produced by radiation, inflammation, ischemia (loss of blood supply) or through excess oxygen inhalation or exposure. As stated previously, free radicals are used by white blood cells to destroy infecting organisms, but can, under circumstances of shock, infection and ischemia, damage or destroy the tissue they were meant to protect.

Free radicals, induced by radiation, oxygen exposure, chemical agents (i.e., alkylating agents, dioxin, paraquat) or white blood cell reactions may be tissue damaging or important to mutational changes associated with aging, radiation or chemotherapy injury, the development of cancer and hyperimmune proliferative disease such as rheumatoid arthritis. In addition, these reactive chemical species can, through oxidation of proteins, enhance the vulnerability of proteins to protease digestion.

In the prior commonly assigned '941, '330, '739 and '408 applications identified above, it was disclosed that PGBx, a fatty acid polymer, is a specific $PLA_2$ inhibitor and prevents the generation of free radicals. $PGB_x$ is capable of inhibiting inflammation induced by $PLA_2$; prevents arachidonate release from human PMNs and vascular endothelium and phospholipids; blocks the synthesis of eicosanoid prostaglandin precursors; protects lipids from auto-oxidation; and decreases endogenous lipid peroxide formation and oxidation of tissue homogenates.

The $PGB_x$ compounds delay aging in houseflies, prolong survival and decrease the age-related pigment in cardiomyocytes, protect paramecia from benzpyrene photoactivation lysis, block the production of superoxide from PMN WBCs, protect the myocardium or myocardial cells from anthracycline or high oxygen tension pro-oxidant injury, block carrageenin and adjuvant induced inflammation and arthritis, block platelet aggregation and blood clotting, and interfere with cytotoxic immune response; block IL-3 leukokine stimulation of mast cell proliferation in vitro, and spontaneous gamma interferon C2 complement release. These compounds can screen out cytotoxic ultraviolet exposure and are systematically and orally active and stable to autoclaving and filtration sterilization.

The general chemical structure of the $PGB_x$ and other oligomers disclosed in the above-identified '330 application has been hypothesized; however, the total defined chemistry required for satisfying regulatory agencies involved in drug development has remained obscure. Accordingly, what is still needed are pharmacologically active materials that are free of compounds having isomeric and/or structural variations.

SUMMARY OF THE INVENTION

The present invention provides both lipid and/or water soluble, pharmacologically active, structurally defined compounds that are $PLA_2$ inhibitors having antioxidant properties and that are relatively pure or purifiable. Thus, the invention provides certain relatively pure bioactive compounds which are polymers and/or oligomers of fatty moieties that inhibit $PLA_2$; and which bind to the $PLA_2$ enzyme. The compounds of the invention possess at least two cis-double bonds to enhance anti-inflammatory and cytoprotective or tissue protective effects of the compounds by making them at least dually active.

The compounds of the invention may be used for treating or prophylactically inhibiting phospholipase mediated injury and/or injury due to oxidation. In a specific sense the invention provides agents for preventing and/or treating inflammation and cell destruction in mammalian tissue and for protection and preservation of biologic material such as food, tissue samples and even wood or cellulose derived products. The compounds of the invention protect phospholipid cell membranes, as well as proteins from the effects of oxidative injury or aging. These compounds also inhibit free radical reactions and thereby stabilize proteins for maintenance of biologic half-life, anti-coagulant activity, and food preservation.

More specifically, the invention provides pharmacologically active, relatively pure or purifiable antioxidant, antiphospholipid compounds that are chemically defined. These compounds are soluble and/or dispersible in a suitable carrier. In accordance with the invention, the compounds have at least two fatty moieties and no active hydroxyl group. Each fatty moiety has from sixteen to twenty carbon atoms and at least one cis-unsaturated double bond. In one preferred form, the compounds of the invention may have an acid group.

In accordance with the invention the compound may be a derivative of ricinoleic acid having the formula

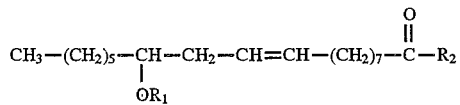

wherein $R_1$ may be an alkoxy group which includes an acid group and $R_2$ may be an alkoxy or alkyl amine group which includes one of the fatty moieties. More particularly, in the foregoing compound $R_2$ may be

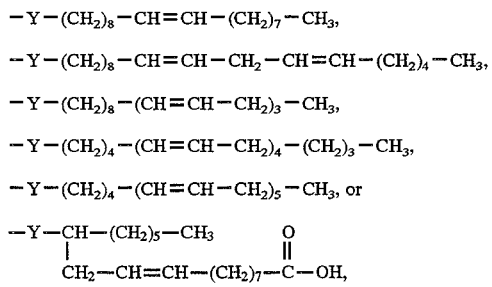

wherein Y is —O— or —NH—.

In an alternative form the compound of the invention may be a derivative of ricinoleic acid having the formula

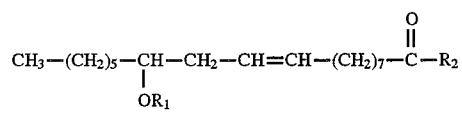

wherein $R_1$ may be an aliphatic group which includes an acid residue and one of the fatty moieties and $R_2$ may be OH or an alkoxy group which includes another one of the fatty moieties. In this form of the invention, when $R_2$ is OH, $R_1$ may be

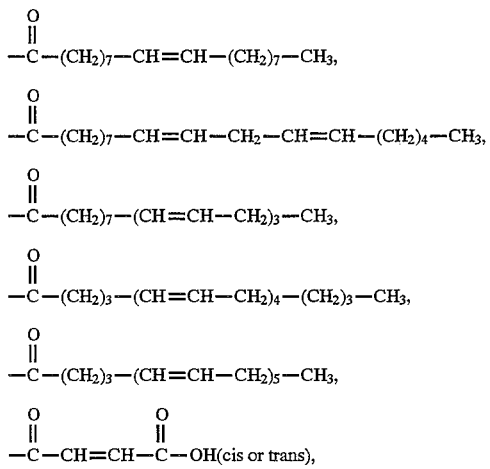

In the foregoing formulas, R may be any organic group which does not interfere with the basic, desirable antioxidant, antiphospholipase characteristics of the compound.

In another alternative form of the invention, the compound may have the formula

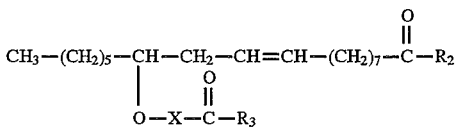

wherein X is a divalent organic moiety and $R_3$ may be OH or an alkoxy group which includes one of the fatty moieties. In this form of the invention $R_3$ may preferably be

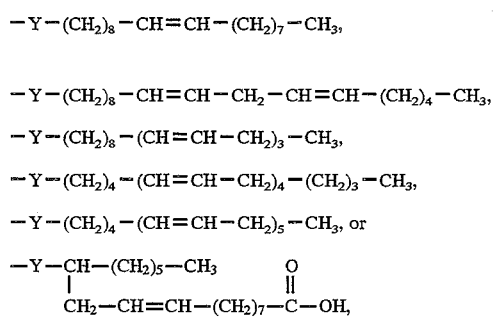

wherein Y is —O— or —NH—, and X may preferably be

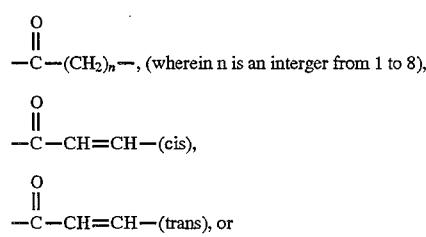

-continued

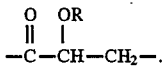

In the foregoing formulas, R may be any organic group which does not interfere with the basic, desirable antioxidant, antiphospholipase characteristics of the compound.

In yet another alternative form of the invention the compound may be a derivative of ricinoleic acid having the formula

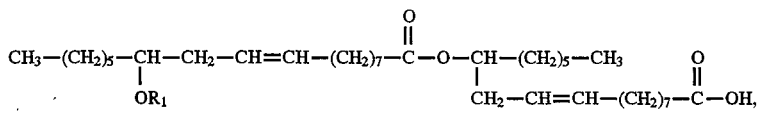

wherein $R_1$ is

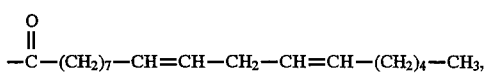

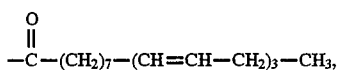

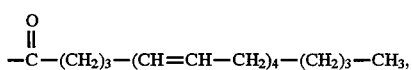

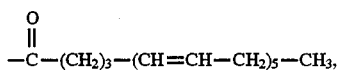

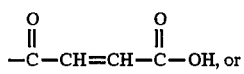

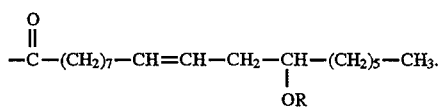

In the foregoing formulas, R may be any organic group which does not interfere with the basic, desirable antioxidant, antiphospholipase characteristics of the compound.

In accordance with the invention, the compound may also have the formula $$R_1\text{—O—X—O—}R_1$$

wherein X is a divalent organic-moiety which includes an active acid group and the $R_1$ groups may be the same or different, and each $R_1$ group may be

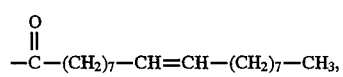

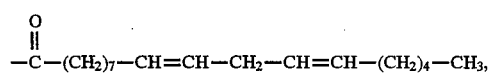

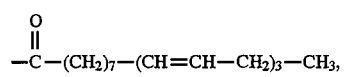

-continued

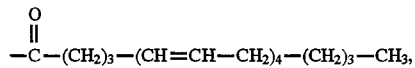

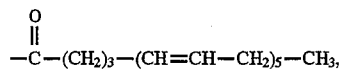

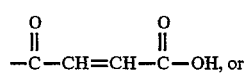

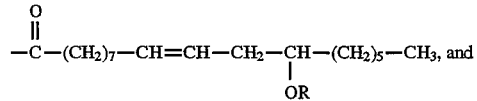

-continued

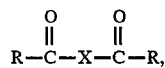

X may be

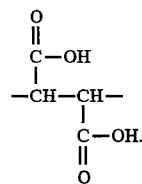

In the foregoing formulas, R may be any organic group which does not interfere with the basic, desirable antioxidant, antiphospholipase characteristics of the compound.

As yet a further alternative, the compound of the invention may have the formula $$\text{R—C(=O)—X—C(=O)—R},$$

wherein X is a divalent organic radical which includes an active acid group, the R groups may be the same or different and each, R may be

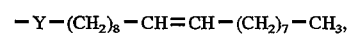

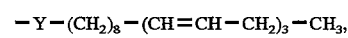

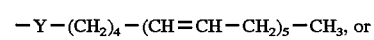

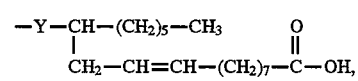

wherein Y is —O— or —NH—, and X may be

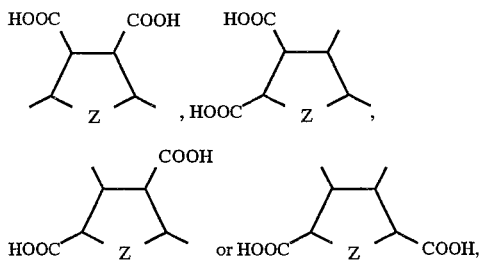

and wherein Z is —O—, —S—, —CH$_2$— or —NH—.

In another alternative form the compounds of the invention may have the formula

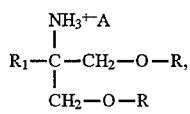

wherein $^-$A is an organic or inorganic anionic moiety; R$_1$ is —CH$_2$—O—R, a hydrogen molecule or a C$_1$ to C$_4$ aliphatic group; and the R groups may be the same or different and each R is a fatty moiety. In this form of the invention, R may be

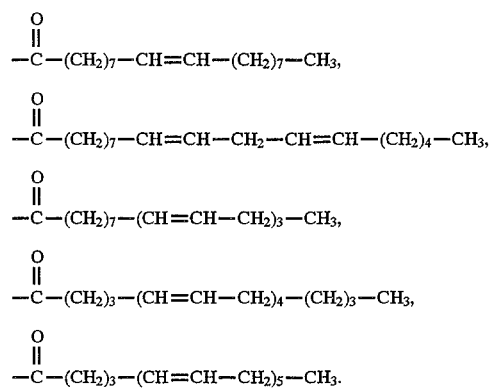

Alternatively, the compounds of the invention may have the formula

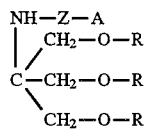

wherein the R groups may be the same or different and each R is a fatty moiety as set forth above. In this form of the invention Z represents a C$_1$ to C$_5$ aliphatic organic moiety and A represents an organic acid moiety.

In another alternative form, the compounds of the invention may have the following structural configuration:

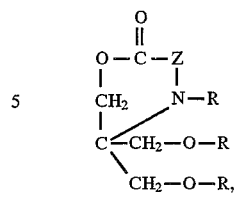

wherein the R groups may be the same or different and each is a fatty moiety, and Z is a C$_1$ to C$_5$ aliphatic organic radical. More specifically, in the foregoing formula, Z may be —CH$_2$— and R may be

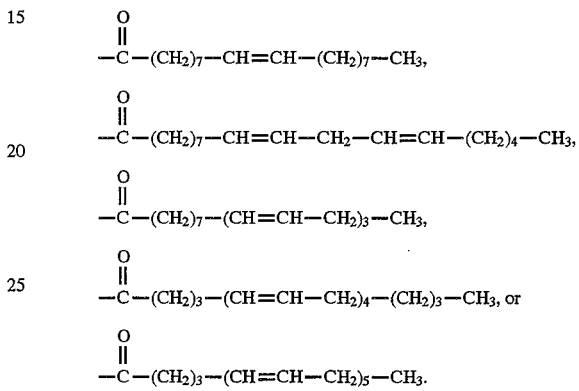

When the foregoing compounds are contacted with NaOH, the lactone ring opens to present the following structural configuration:

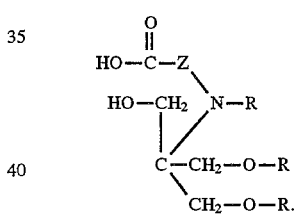

The compounds of the invention may also have the following structural formula

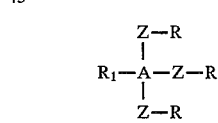

wherein A is a C$_1$ to C$_7$ aliphatic moiety, R$_1$ is —Z—R, a C$_1$–C$_4$ alkyl group, a nitro group, an amino group, a carboxylic acid group, a sulfonic acid group, or a hydrogen atom, said Z groups are the same or different and each is —O— or —NH—, and each R is a fatty moiety as described above.

DESCRIPTION OF THE PREFERRED EMBODIMENTS

Figure 1:
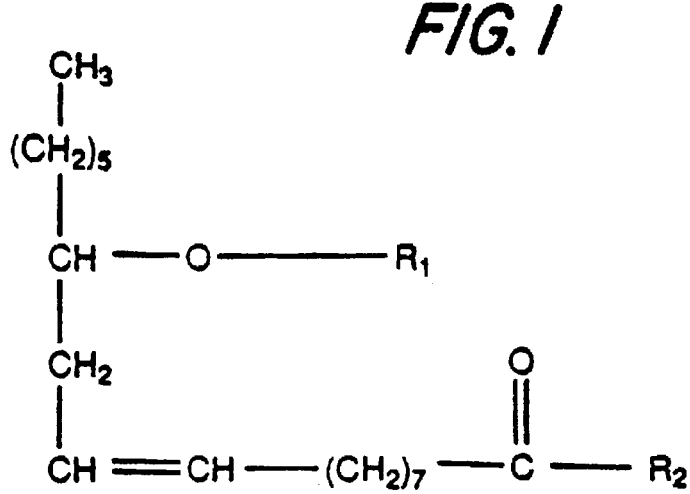
FIGS. 1 through 7 illustrate structural configurations and reaction schemes for preparing various embodiments of the novel cytoprotective, pharmacologically antioxidant, antiphospholipase active compounds of the invention.

In previous work by Ballou and Cheng (Proc. Natl. Acad. Sci. 80: 5203–5207, 1983, IBID 82: 371–375, 1985) and Marki and Franson (Biochem. Biophys. Acta. 879:149–156, 1986) it has been reported that cis-unsaturated, but not saturated fatty acids, inhibit in vitro $PLA_2$ activities derived from human platelets and human polymorphonuclear leucocytes (PMNs). $PLA_2$ activity has been shown to be inhibited by oleic, linoleic, and arachidonic acids to approximately the same extent indicating that the presence of a single cis-double bond is as inhibitory as multiple cis-double bonds. In contrast, neither fatty acids containing trans-double bonds nor methyl esters of cis-unsaturated fatty acids are inhibitory of $PLA_2$ activity. Thus, it has been hypothesized that the preferred structural characteristics for inhibition of in vitro $PLA_2$ activity by unesterified fatty acids include at least one cis-double bond. As was illustrated above, oleic acid inhibits in vitro $PLA_2$ activity due to the presence of a single cis-double bond at the C-9 position. However, recent studies have demonstrated that hydroxylation at the C-12 carbon atom to produce 12-hydroxy-oleic acid (ricinoleic acid) eliminates the inhibitory activity. Thus, despite the fact that the cis-double bond is intact, this hydroxylation substitution converts an inhibitory fatty acid to a non-inhibitory fatty acid. In fact, ricinoleic acid is a potent inflammatory agent and is used as such in experimental models or as an effective ingredient of caster oil's cathartic action.

In support of this, a similar change occurs with arachidonic acid, a 20 carbon fatty acid with 4 cis-double bonds. This compound is an inhibitory cis-polyunsaturated fatty acid which is converted to prostaglandin $B_1$ ($PGB_1$) via the cyclo oxygenase pathway. The product $PGB_1$ is markedly less inhibitory than the precursor arachidonic acid (by at least 2 orders of magnitude) presumably because it has acquired a hydroxyl group.

Based on the above, it is evident that oxidative reactions can neutralize the $PLA_2$ inhibitory effect of cis-unsaturated fatty acids. In fact, hydroxylation can make these fatty acids pro-inflammatory. Of physiologic and pharmacologic importance to this, data has been presented in the '330 application identified above to show that pro-oxidation of the sarcoplasmic reticulum of muscle predisposes the tissue to phospholipase degradation. The oxidation of phospholipid membranes enhances the vulnerability of cell membranes to phospholipase degradation. Phospholipid membranes that have been oxidized at particular sites may appear intact and maintain functional activity, but their oxidation makes them vulnerable to degradation and destruction by $PLA_2$ or other phospholipases, from endogenous or exogenous sources.

The reversal of $PLA_2$ inhibition by radical-mediated oxidation of cis-unsaturated fatty acids may be an important means by which in situ $PLA_2$s are activated to mediate tissue inflammation, differentiation, and cell death. In support of this, it has been determined that arachidonic acid binds directly to purified $PLA_2$ from snake venom. Moreover, when the arachidonic acid is peroxidized by exposure to air at 37° C., the arachidonic acid remains bound to the isolated $PLA_2$ but no longer inhibits in vitro $PLA_2$ activity. These results are the focus of the discovery of the fact that cellular $PLA_2$s are fatty acid binding proteins, and when the bound fatty acid is cis-unsaturated, the $PLA_2$ will be inhibited. Furthermore, when cis-unsaturated fatty acids are oxidized, $PLA_2$ enzymic activity is restored, thereby increasing the level of "effective" enzyme. The net result when fatty acids are oxidized is an apparent activation of $PLA_2$ to induce membrane injury, inflammation, cytotoxicity and cell death. This shift from inactive to active form of $PLA_2$ signals the onset of the loss of phospholipid membrane structure.

In related studies, Jung et al. (Biochem. Biophys. Res. Commun. 130:559–566, 1985) have shown that the specific hydroxylation of carbon 15, but not carbon 5 or 12, of arachidonic acid esterified at the 2-position of phosphatidylcholine, increased pancreatic $PLA_2$ mediated hydrolysis of the phospholipid by 170%. Thus, oxidative reactions of cis-unsaturated fatty acids not only "activate" $PLA_2$ enzyme function by altering inhibitory fatty acids, but also can increase the susceptibility of the substrate phospholipid to hydrolysis induced by the enzyme.

The observations illustrating the enhanced vulnerability of phospholipid membranes to phospholipase following oxidative and radical mediated changes in cell membranes and/or cis-fatty acids have been employed in accordance with the present invention in the design of novel anti-inflammatory and cytoprotective agents. The invention thus provides a biochemical and synthetic organic approach to controlling the expression of $PLA_2$ enzymes and is vital to the maintenance of membrane structure.

It is important to the understanding of the present disclosure to recognize that the number of available methylene interrupted cis-unsaturated double bonds is directly related to the susceptibility of fatty acids to oxidation. This governs the ability of cis-unsaturated fatty acids to act as anti-oxidants. This property, in conjunction with the anti-$PLA_2$ activity of the fatty moiety compounds of the invention, markedly expands the scope of the anti-inflammatory and cytoprotective activity of the new agents disclosed herein. It is the property of the dual action of these compounds, i.e., their action as $PLA_2$ inhibitors and their combined anti-oxidant activity, that provides the spectrum of anti-inflammatory activity in model systems that have direct applicability to cytoprotection and the control of inflammation and pathophysiology.

In summary, a single cis-double bond in a fatty moiety compound is sufficient to inhibit $PLA_2$ activity in vitro and in situ. The addition of multiple double bonds provides the additional value of an increase in potent anti-oxidant activity along with $PLA_2$ inhibitory action. The present invention thus provides compounds characterized by both anti-$PLA_2$ and anti-oxidant activity to thereby maximize the anti-inflammatory and cytoprotective action which is the key to the clinical value of the compounds of the invention.

In addition to inhibiting $PLA_2$ activity, the anti-oxidant action of these compounds protects proteins that become increasingly vunerable to attack by proteases due to oxidation. Thus, the cytoprotective $PLA_2$ inhibitors of the invention, which have anti-oxidant activity as well, have value both in stabilizing membrane phospholipid and in inhibiting or preventing protein degradation or denaturation.

In accordance with the invention, the cytoprotective anti-inflammatory compounds:

(1) bind to the $PLA_2$ enzyme;
(2) are capable of being continuously hydroxylated to remove the inhibitory action and activate the enzyme without removal of the component from its $PLA_2$ binding site;
(3) are compounds containing fatty moieties which may have a free acid function or at least are preferably ionizable for water solubility and enhanced $PLA_2$ inhibition;

(4) include cis-double bonds in the fatty moieties to obtain the best $PLA_2$ inhibition; and (5) possess anti-inflammatory activity as a result of inhibiting free radical activity.

As reported in the cross-referenced patent applications identified above, prior studies have shown that polymers of $PGB_1$, but not the monomer $PGB_1$ itself, provide broad protection in a wide range of cell and tissue injury models. In contrast to the present disclosure, no basic mechanism underlying this generalized protective effect was identified. But it was clear from these previous studies that polymers or oligomers were more effective than monomers and that a free carboxyl function in the polymer may be desirable for optimum protective activity.

In recent studies it has been determined that polymers of $PGB_1$ inhibit a broad range of $Ca^{++}$-dependent $PLA_2$s, including snake, bee, and scorpion venom, and human $PLA_2$s derived from synovial fluid, PMNs, platelets, plasma, sperm, endometrium, and herniated discs. At 10 µM concentrations, $PGB_1$ (monomer) was not inhibitory while the dimer had ½ the maximal inhibitory activity. The inhibitory activity of the trimer is less than that of tetramer while the activity of the latter is equal to that of $PGB_x$. Thus, polymerization of prostaglandin $B_1$, a metabolite of the cis-polyunsaturated fatty acid arachidonate, generates inhibitors of $PLA_2$s.

Similarly, as reported in the cross-referenced applications, polymers of $PGB_1$ are equally effective at inhibiting the release of arachidonic acid and platelet activating factor from prelabelled human PMNS and endothelial cells which are reactions critical to the inflammatory response of these cells and which are mediated by endogenous $PLA_2$ activity.

Of particular relevance to the present disclosure, is the fact that polymers of $PGB_1$ also have potent anti-oxidant activity. Arachidonic acid, as noted above, contains 4 cis-unsaturated, methylene interrupted, double bonds which are particularly susceptible to oxidation. When arachidonic acid is converted to prostaglandin $B_1$ by cyclo-oxygenase, an enzyme mediated oxygenation, two of the four original cis-double bonds are retained. These bonds remain in a methylene-interrupted configuration, which is the optimal orientation for their oxidation.

The compounds of the present invention block arachidonic acid release from human PMNs and endothelial cells, a reaction mediated by cellular $PLA_2$ activity. Thus, the compounds of the invention are potent, reversible enzyme-targeted $PLA_2$ inhibitors, and as such these agents inhibit the pro-inflammatory response of the human PMN and other inflammatory cells by inhibition of cellular $PLA_2$ activity. In addition, the compounds of the invention inhibit free radical activity in cells and tissue involved in the inflammatory process.

The compounds of the invention also are effective anti-oxidants. Oxidation of phospholipid and arachidonic acid is inhibited in a dose-dependent manner. This property not only protects membranes from radical mediated injury to stabilize function, but also prevents the preferential hydrolysis of oxidized phospholipid by cellular phospholipases. These results suggest that the compounds of the invention act to minimize inflammation at its onset and will also interrupt the process in progress.

The ability of cis-unsaturated fatty moiety compounds to prevent oxidation of proteins will also suppress the expression of cell proteases by maintaining levels of endogenous protease inhibitors. These inhibitors, such as $\alpha$-1-anti-trypsin, are major components of plasma and their inhibitory activity is abolished by free radical mediated oxidation of —SH groups. The anti-oxidant activity of the cis-unsaturated fatty moiety compounds of the present invention stabilizes $\alpha$-1-anti-trypsin via the anti-oxidant action. Thus, the anti-oxidant activity of cis-unsaturated fatty moiety compounds regulates the expression of both lipolytic and proteolytic enzymes (i.e., elastase) by preventing the oxidation of both substrate and endogenous inhibitors.

The 12-hydroxylation of oleic acid yields ricinoleic acid. Thus, an inhibitory fatty acid is converted into a non-inhibitory hydroxylated derivative. However, the —OH moiety can be used to generate inhibitory compounds. The hydroxylated derivatives thus provide building block precursors for the synthesis of active cytoprotective agents with $PLA_2$ inhibiting activity. Indeed, when ricinoleate is polymerized by heat in sulfuric acid, the crude unfractionated product inhibits in vitro and in situ $PLA_2$ activity.

In effect, the inactive non-inhibiting monomers are converted to extremely active $PLA_2$ inhibitors. Moreover, active pro-inflammatory mediators are converted structurally to provide anti-inflammatory compounds.

$PLA_2$ inhibitors such as derivatives of ricinoleic acid that do not have significant anti-oxidant activity have limited anti-inflammatory effect. The presence of the unsaturated bonds of the cis-unsaturated fatty moiety compounds enhances the anti-inflammatory activity. This indicates that inflammatory reactions may vary in their characteristics wherein some inflammatory response can be inhibited or attenuated by $PLA_2$ inhibition alone, while other reactions require anti-oxidant activity along with $PLA_2$ inhibition. Thus, in accordance with the invention, to obtain broad spectrum anti-inflammatory action, the dual action of anti-$PLA_2$ and anti-oxidant activity is preferred. Polyunsaturated compounds constructed from unsaturated fatty acids and other unsaturated fatty compounds provide potent anti-oxidant activity as well as anti-$PLA_2$ action.

In a general sense, the invention provides pharmacologically active, antiphospholipase compounds that are chemically defined and purifiable. Preferably the compounds of the invention are water soluble antioxidants. From a functional viewpoint, the preferred compounds have at least two fatty moieties and no active hydroxy group. Each fatty moiety should preferably have sixteen to twenty carbon atoms and at least one cis-unsaturated double bond. The compounds may also have at least one active acid group. In one preferred form, the compound may be a derivative of ricinoleic acid having a structural configuration as set forth in FIG. 1 of the drawings where $R_1$ is an alkoxy group which includes an active acid group and $R_2$ is an alkoxy group which includes one of the fatty moieties. In one case the $R_1$ moiety may be obtained by esterification of the 12-position hydroxy group of ricinoleic acid with an acid group of a divalent acid such as sebacic acid, fumaric acid, maleic acid, oxalic acid or succinic acid, and the $R_2$ moiety may be obtained by esterification of the 1-position carboxy group of ricinoleic acid with the hydroxyl group of another ricinoleic acid molecule or of some other cis-unsaturated fatty alcohol such as, for example, oleyl alcohol, linoleyl alcohol, linolenyl alcohol, arachidonyl alcohol or cis-5, 8, 11, 14, 17-eicosapentaenoyl alcohol. Alternatively, the $R_2$ moiety may be obtained by amidification of the 1-position carboxy group of ricinoleic acid with the amine group of a cis-unsaturated fatty amine such as oleyl amine, linoleyl amine, linolenyl amine, arachidonyl amine or cis-5, 8, 11, 14, 17-eicosapentaenoyl amine. Thus, for example, $R_2$ may be a moiety having one of the following configurations:

—Y—(CH$_2$)$_8$—CH=CH—(CH$_2$)$_7$—CH$_3$,
—Y—(CH$_2$)$_8$—CH=CH—CH$_2$—CH=CH—(CH$_2$)$_4$—CH$_3$,
—Y—(CH$_2$)$_8$—(CH=CH—CH$_2$)$_3$—CH$_3$,
—Y—(CH$_2$)$_4$—(CH=CH—CH$_2$)$_4$—(CH$_2$)$_3$—CH$_3$,
—Y—(CH$_2$)$_4$—(CH=CH—CH$_2$)$_5$—CH$_3$, or $$-Y-\underset{\underset{CH_2-CH=CH-(CH_2)_7-\overset{O}{\overset{\|}{C}}-OH,}{|}}{CH}-(CH_2)_5-CH_3$$

wherein Y may be —O— or —NH—.

Alternatively, the compound may have the generic structural formula as set forth in FIG. 1; however, in this case R$_1$ may be an aliphatic group which includes an active acid group and one of the cis-unsaturated fatty moieties and R$_2$ may be either a hydroxy group or an alkoxy group which includes fatty moieties. In this alternative case, When R$_2$ is a hydroxy group R$_1$ may be derived by esterification of the 12-position hydroxy group of the ricinoleic acid, with, for example, the acid group of oleic acid, linoleic acid, linolenic acid, arachidonic acid or cis-5, 8, 11, 14, 17-eicosapentaenoic acid. Thus, in this case, R$_1$ may be a fatty moiety having one of the following configurations:

$$-\overset{O}{\overset{\|}{C}}-(CH_2)_7-CH=CH-(CH_2)_7-CH_3,$$

$$-\overset{O}{\overset{\|}{C}}-(CH_2)_7-CH=CH-CH_2-CH=CH-(CH_2)_4-CH_3,$$

$$-\overset{O}{\overset{\|}{C}}-(CH_2)_7-(CH=CH-CH_2)_3-CH_3,$$

$$-\overset{O}{\overset{\|}{C}}-(CH_2)_3-(CH=CH-CH_2)_4-(CH_2)_3-CH_3, \text{ or}$$

$$-\overset{O}{\overset{\|}{C}}-(CH_2)_3-(CH=CH-CH_2)_5-CH_3.$$

With reference to the structural configuration presented in FIG. 1, in another alternative embodiment R$_1$ may be $$-X-\overset{O}{\overset{\|}{C}}-R_3$$

wherein X is a divalent organic moiety and R$_3$ is OH or an alkoxy group that includes a cis-unsaturated fatty moiety. When R$_3$ is OH, either X or R$_1$ must include a cis-unsaturated fatty moiety. On the other hand, in accordance with an alternative embodiment of the invention, R$_3$ may be a moiety having one of the following configurations:

—Y—(CH$_2$)$_8$—CH=CH—(CH$_2$)$_7$—CH$_3$,
—Y—(CH$_2$)$_8$—CH=CH—CH$_2$—CH=CH—(CH$_2$)$_4$—CH$_3$,
—Y—(CH$_2$)$_8$—(CH=CH—CH$_2$)$_3$—CH$_3$,
—Y—(CH$_2$)$_4$—(CH=CH—CH$_2$)$_4$—(CH$_2$)$_3$—CH$_3$,
—Y—(CH$_2$)$_4$—(CH=CH—CH$_2$)$_5$—CH$_3$, or $$-Y-\underset{\underset{CH_2-CH=CH-(CH_2)_7-\overset{O}{\overset{\|}{C}}-OH,}{|}}{CH}-(CH_2)_5-CH_3$$

wherein Y is —O— or —NH—.

In the foregoing embodiment, when R$_1$ of the structure of FIG. 1 is $$-X-\overset{O}{\overset{\|}{C}}-R_3,$$

X, for example, may be one of the following divalent moieties:

$$-\overset{O}{\overset{\|}{C}}-(CH_2)_n-, \text{ (wherein n may be an integer from 1 to 8),}$$

$$-\overset{O}{\overset{\|}{C}}-CH=CH- \text{ (cis),}$$

$$-\overset{O}{\overset{\|}{C}}-CH=CH- \text{ (trans), or}$$

$$-\overset{O}{\overset{\|}{C}}-\underset{\underset{}{\overset{|}{CH}}}{\overset{\overset{OR}{|}}{}}-CH_2-.$$

Figure 3:
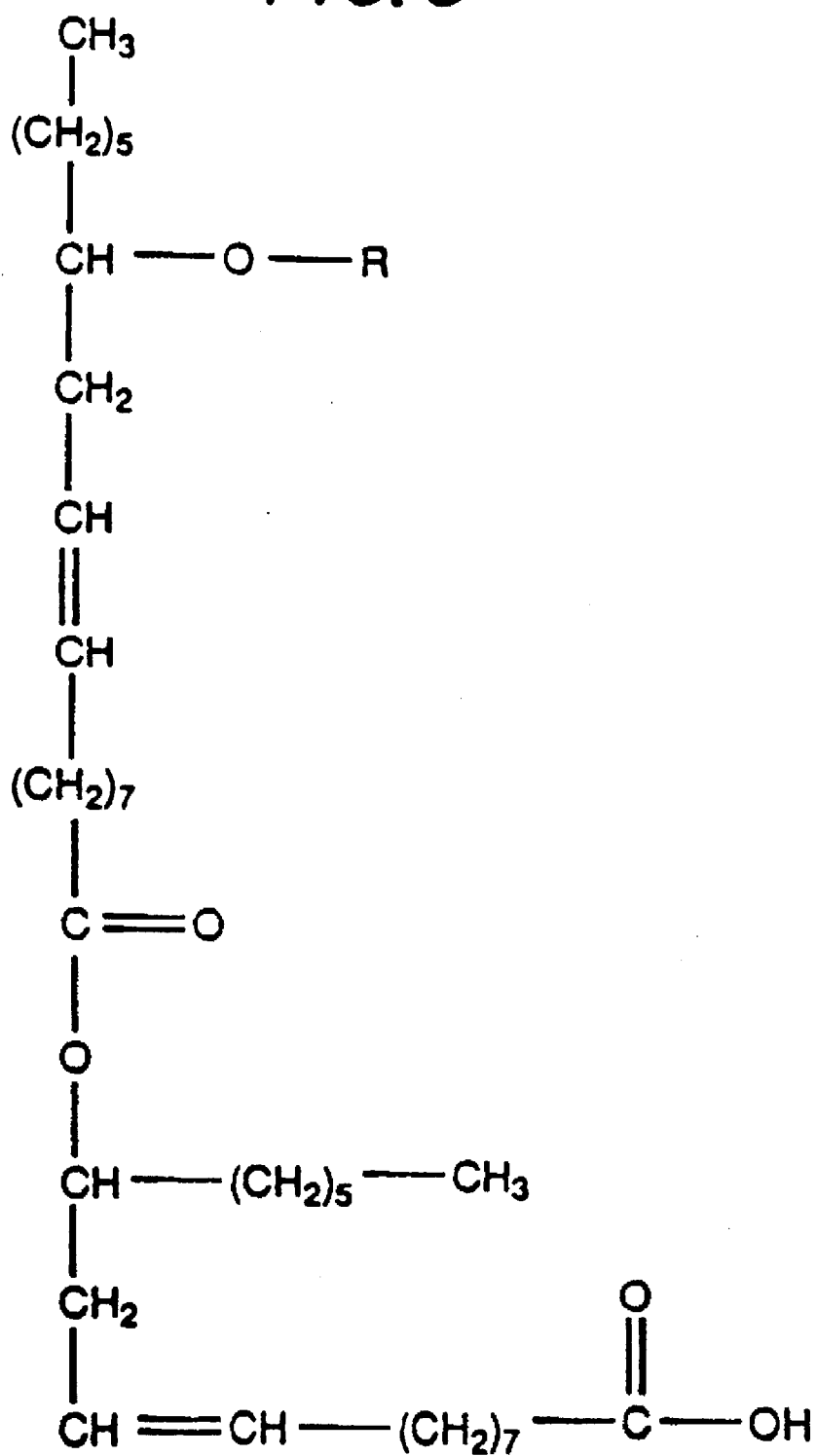

When R$_2$ of the FIG. 1 structure is derived by esterifying the 12-position OH of ricinoleic acid with the 1-position carboxy group of another molecule of ricinoleic acid, the resultant structure will be as shown in FIG. 3. In this case the OH at the 12-position of the second ricinoleic acid molecule must be rendered non-inhibitory. This may be done by esterification to cause R to be, for example, one of the following moieties:

$$-\overset{O}{\overset{\|}{C}}-(CH_2)_7-CH=CH-(CH_2)_7-CH_3,$$

$$-\overset{O}{\overset{\|}{C}}-(CH_2)_7-CH=CH-CH_2-CH=CH-(CH_2)_4-CH_3,$$

$$-\overset{O}{\overset{\|}{C}}-(CH_2)_7-(CH=CH-CH_2)_3-CH_3,$$

$$-\overset{O}{\overset{\|}{C}}-(CH_2)_3-(CH=CH-CH_2)_4-(CH_2)_3-CH_3,$$

$$-\overset{O}{\overset{\|}{C}}-(CH_2)_3-(CH=CH-CH_2)_5-CH_3,$$

$$-\overset{O}{\overset{\|}{C}}-\overset{O}{\overset{\|}{C}}=C-\overset{O}{\overset{\|}{C}}-OH, \text{ or}$$

$$-\overset{O}{\overset{\|}{C}}-(CH_2)_7-CH=CH-CH_2-\underset{\underset{OR}{|}}{CH}-(CH_2)_5-CH_3.$$

In accordance with another embodiment of the invention, the structural configuration of the compound may be

R$_1$—O—X—O—R$_1$ wherein X is a divalent organic moiety which may include an active acid group and the R$_1$ groups may be the same or different and each may, for example, be one of the following moieties:

$$-\overset{O}{\overset{\|}{C}}-(CH_2)_7-CH=CH-(CH_2)_7-CH_3,$$

-continued

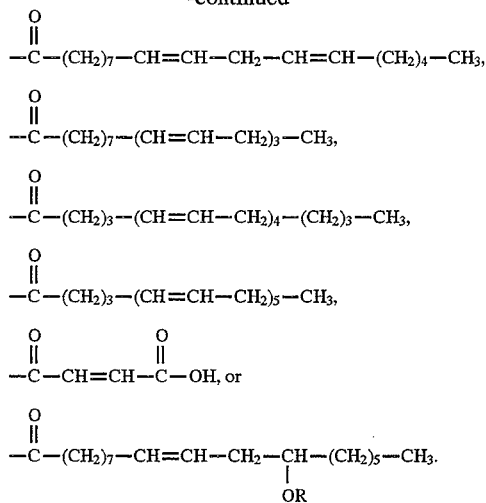

In this form of the invention, X may be derived by esterification of the hydroxy group of tartaric acid whereby X will have the following structural configuration:

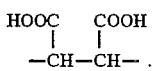

Figure 5:
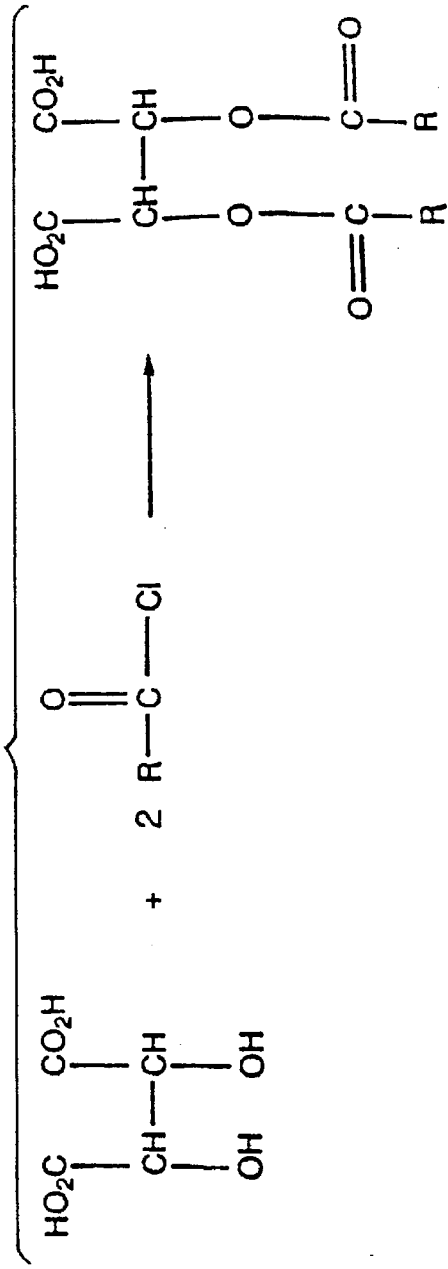

An appropriate reaction scheme for this procedure is illustrated in FIG. 5. Each

moiety in the FIG. 5 compound is represented by an $R_1$ group in the compound

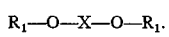

In yet another alternative form, the compounds of the invention may have the structure

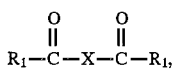

wherein X is a divalent organic moiety which may include an active acid group and the $R_1$ groups, which may be the same or different, may, for example, be one of the following moieties:

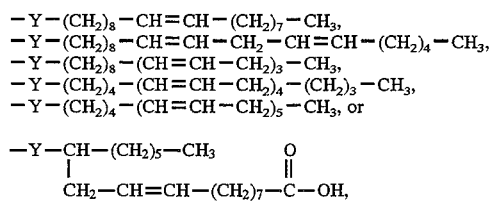

wherein Y is —O— or —NH—.

In this embodiment, X may be

Figure 4:
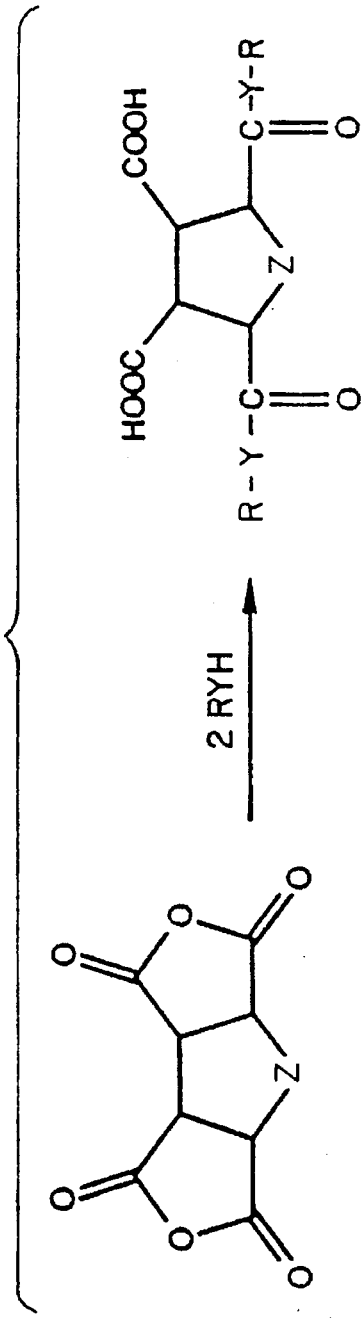

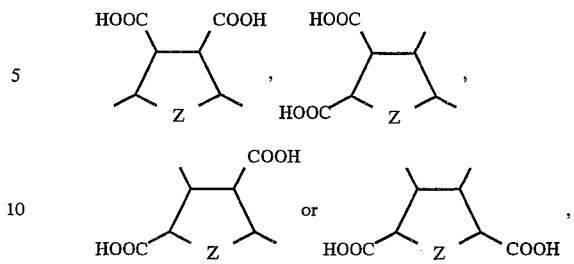

wherein Z may be —O—, —S—, —CH$_2$— or —NH—. The compounds of this embodiment may be prepared using a reaction scheme as illustrated in FIG. 4 where the produced compound is shown as having carboxyl groups at the 2 and 3 positions of the ring. However, as will be appreciated by those skilled in the art, the reaction scheme of FIG. 4 may be conducted so as to provide any one of several isomeric compounds, i.e., with the carboxyl groups at the 2 and 3 positions as shown or alternatively with the carboxyl groups at the 1 and 2 positions, at the 1 and 3 positions or at the 1 and 4 positions. Each R—Y— moiety in the FIG. 4 compound is represented by an $R_1$ group in the compound

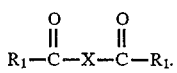

Figure 2:
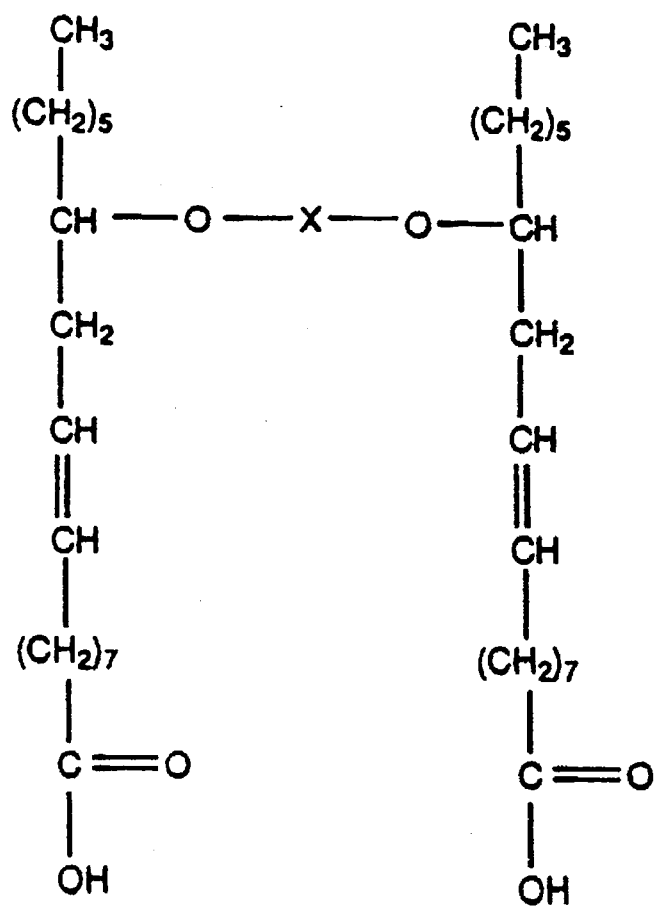
Figure 6:
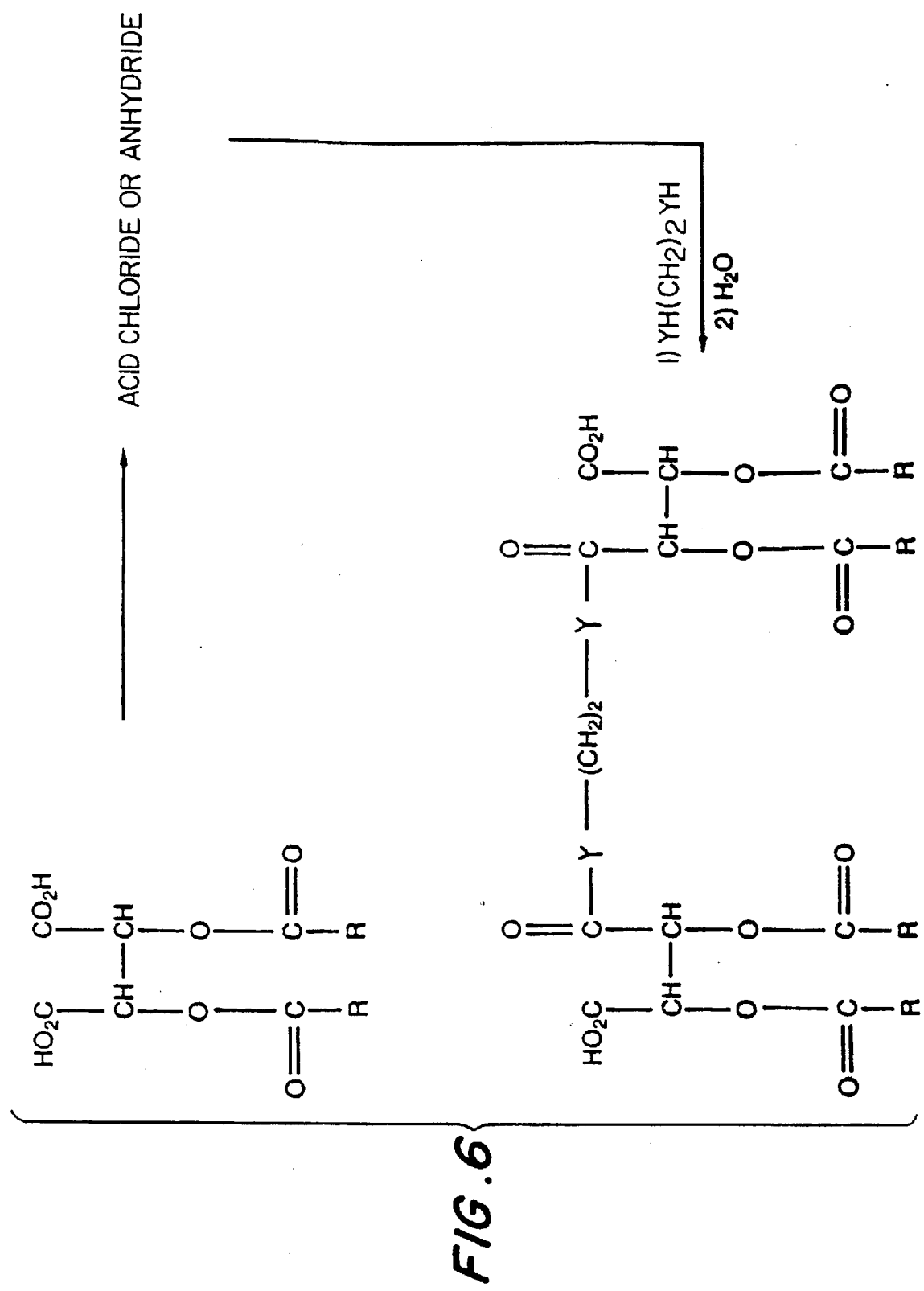
Figure 7:
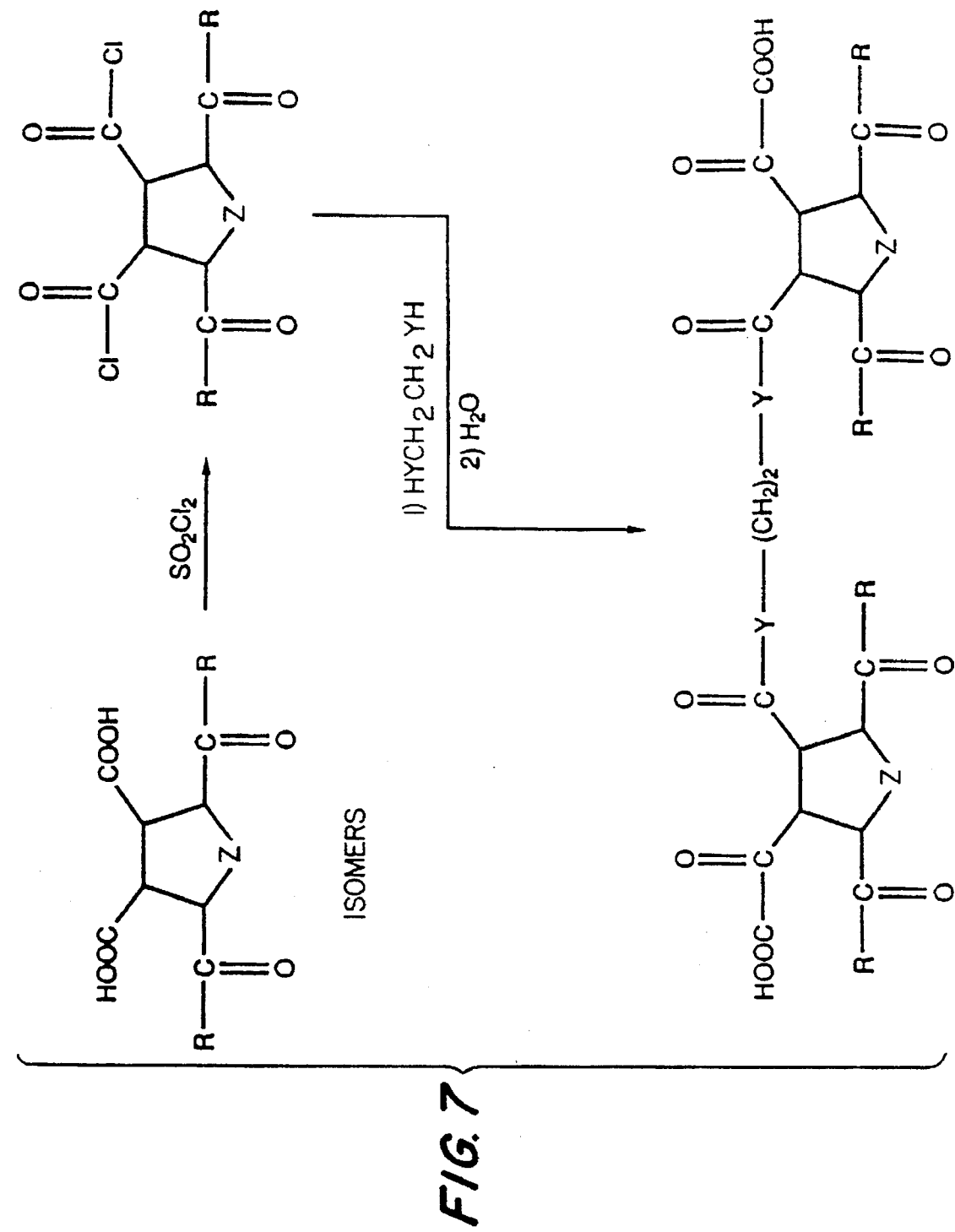

The invention contemplates a variety of configurations including, for example, dimers, trimers and tetramers. Dimers are illustrated in FIGS. 1, 2, 4 and 5, trimers are illustrated in FIGS. 1 and 3 and tetramers are illustrated in FIGS. 6 and 7. The structures illustrated in FIGS. 1 and 3 and the reaction schemes of FIGS. 4 and 5 have been discussed above. The structure illustrated in FIG. 2 is a dimer of ricinoleic acid prepared by esterifying the 12-position hydroxy groups of two molecules of ricinoleic acid with the carboxy groups of a diacid such as sebacic acid, fumaric acid, maleic acid, oxalic acid or succinic acid, for example.

With reference to FIG. 6, the compounds produced in accordance with FIG. 5 may be linked together by esterification through one of the free acid groups. Thus, the acid groups may be converted to acid chloride groups and reacted with hydroxy or amine groups of a divalent compound having the form

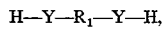

wherein Y is —O— or —NH— and $R_1$ is a divalent, preferably aliphatic, organic moiety. As before, the R groups of the compound formed as illustrated in FIG. 6 may be the same or different and may preferably be cis-unsaturated fatty moieties.

The reaction scheme illustrated in FIG. 7 may employ any one of the isomeric compounds that may be formed in accordance with the reaction scheme of FIG. 4 as discussed above. Thus, the free acid groups of one of the FIG. 4 isomeric compounds are converted to the acid chloride or anhydride and esterified with the hydroxy or amino groups of a bivalent organic moiety.

In each case, the compounds of the invention include at least two cis-unsaturated $C_{16}$–$C_{20}$ straight chain fatty moieties and have no active hydroxy group. Desirably, each compound may also include at least one active acid group.

The novel water soluble and/or lipid soluble pharmacologically active, pure or purifiable antioxidant, antiphospholipase compounds provided in accordance with principles and concepts of the invention may be prepared as outlined in the following specific examples.

EXAMPLE I

Diricinoleic Acid Fumarate Diester (RAFARA)

In a 500 ml single-necked round-bottom flask, 5.0 g of crude ricinoleic acid (Tokyo Kasei Co., 80% content) is dissolved in 180 ml of $CH_2Cl_2$ containing 2.8 g of $NaHCO_3$. 6.5 ml of fumaryl chloride (42 mmoles) is added dropwise over 2 minutes under vigorous stirring by a magnetic stirrer at room temperature. The mixture is stirred for 88 hours and then 100 ml of 5% aqueous $NaHCO_3$ is added slowly to the reaction flask while cooling with an ice bath. The mixture is poured into a 1000 ml beaker containing 300 ml of 2% $NaHCO_3$. Upon standing overnight, the $CH_2Cl_2$ layer is separated and acidified with 12N HCl until the pH is 1. The $CH_2Cl_2$ solution is washed three times with distilled $H_2O$, dried over anhydrous $MgSO_4$, and the $CH_2Cl_2$ is removed by rotoevaporation at 35° C. A yellow oily material is obtained.

This crude product is purified by column chromatography (Aldrich 230–400 mesh 1×70 cm) with petroleum ether-ethyl acetate (6:4) as eluent. Under set conditions, dimer (I) is collected with one spot shown on silica gel TLC plate, $R_f$ 0.26, (Baker-flex Silica Gel LB-F, 6:4 petroleum ether (bp 50°–110° C.)-ethyl acetate).

The product, which may be called RAFARA, has the following structural configuration:

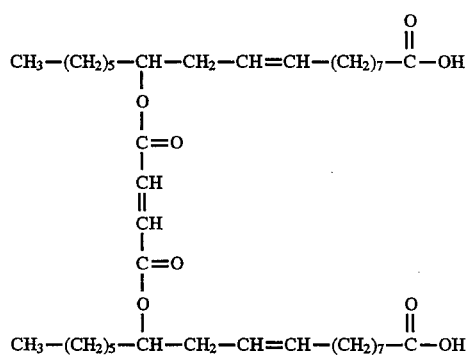

EXAMPLE II

Ricinoleic acid—Linoleic Acid Ester (RALA)

Ricinoleic acid 1.0 g (3.4 mmoles, Sigma) is dissolved in 10 ml of propylene oxide and placed in a 100 ml round-bottomed, single-necked flask equipped with a Teflon-coated magnetic stirring bar. The solution is cooled to 0° C. on an ice-water bath, and 2.0 g linoleoyl chloride (6.8 mmoles) in 5 ml of anhydrous methylene chloride is added dropwise. The mixture is warmed to room temperature and stirred for 3 days. After removing the solvent by rotoevaporation, the residue is dissolved in 150 ml of methylene chloride. The mixture is washed with 200 ml of 5% aqueous $NaHCO_3$ three times, and then the methylene chloride layer is separated and dried over anhydrous magnesium sulfate. After removal of the methylene chloride, the crude product is purified by column chromatography using silica gel (Aldrich, 230–400 mesh, 1.0×70 cm). Elution is performed using 8:2 chloroform-ethyl acetate as the developing solvent. The product (RALA) obtained shows one spot on TLC, $R_f$ 0.54 (Baker-flex Silica Gel 1B-F, 8:2 chloroform-ethyl acetate) and has the following structural configuration:

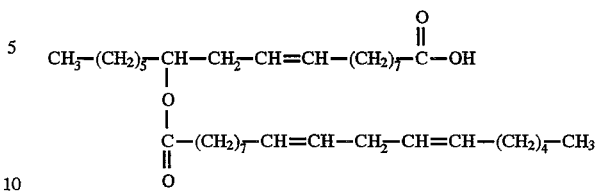

EXAMPLE III

Ricinoleic Acid—Oleic Acid Ester (RAOA)

0.5 g ricinoleic acid (1.7 mmoles, Sigma) is dissolved in 6 ml of anhydrous $CH_2Cl_2$ and placed in a 100 ml round-bottomed, single-necked flask equipped with a Teflon-coated magnetic stirring bar. After addition of 0.15 g pyridine (1.7 mmoles), the solution is cooled to 0° C. on an ice-water bath, and 0.5 g oleoyl chloride (1.7 mmoles, Sigma) in 4 ml of anhydrous $CH_2Cl_2$ is added dropwise. The mixture is warmed to room temperature and stirred for 2 days. The solvent is removed by rotoevaporation and 500 ml of anhydrous ether is added to the residue. The white precipitate formed is removed by filtration. Ether is removed by rotoevaporation and 50 ml of anhydrous $CH_2Cl_2$ is added to the oily residue. The $CH_2Cl_2$ layer is washed three times with 50 ml portions of 5% aqueous $NaHCO_3$. The $CH_2Cl_2$ layer is dried and the solvent removed by rotoevaporation. The crude product is purified by column chromatography using silica gel (Aldrich, 230–400 mesh, 1.0×55 cm). Elution is performed using 8:2 petroleum ether (bp 50°–100° C.)-ethyl acetate as the developing solvent. The fractions containing the product are combined and the solvent is evaporated. The product shows only one spot on TLC, $R_f$ 0.51 (Baker-flex Silica Gel 1B-F, 8:2:1 petroleum ether-ethyl acetate-acetic acid).

The product RAOA has the following structural configuration:

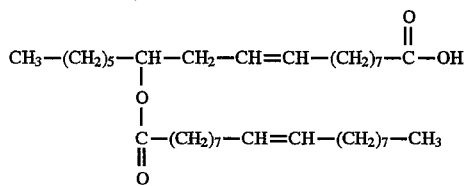

EXAMPLE IV

Oleyl Alcohol-Ricinoleate-Fumaric Acid Diester (OA1RAFA)

2.2 g of crude ricinoleic acid-oleyl ester, (4 mmoles, based on the assumption that the material is pure, Tokyo Kasei Co.), is dissolved in 10 ml of anhydrous $CH_2Cl_2$ and 10 ml of propylene oxide, and placed in a 100 ml round-bottomed three-necked flask equipped with a drying tube and a Teflon-coated magnetic stirring bar. The solution is cooled to 0° C., and 3.04 g fumaryl chloride (20 mmoles) in 10 ml of anhydrous $CH_2Cl_2$ is added dropwise from an additional funnel over 10 minutes. The reaction mixture is warmed to room temperature and stirred for three days. After removal of solvent by rotoevaporation, the residue is dissolved in 100 ml of ethyl acetate. The ethyl acetate layer is washed 5 times with 75 ml portions of 5% aqueous $NaHCO_3$. The ethyl acetate layer is separated and dried over anhydrous sodium sulfate. Ethyl acetate is removed by rotoevaporation to yield a brownish oily residue. This crude product is purified by column chromatography using silica gel (Aldrich, 230–400 mesh, 1.0×55 cm). Elution is performed using 8:2 petroleum ether (bp 50°–110° C.)-ethyl acetate as developing solvent. The product shows only one spot on TLC, $R_f$ 0.39 (Baker-flex Silica Gel 1B-F, 8:2 petroleum ether-ethyl acetate).

The product OA1RAFA has the following structural configuration:

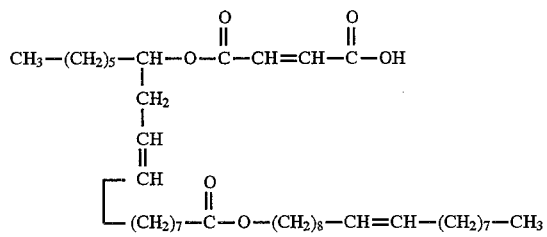

EXAMPLE V

Ricinoleic Acid—Sebacyl Ester (RISE-1)

5 g of ricinoleic acid (16.75 mmole, Sigma) is added to a mixture of 200 ml of methylene chloride and 2.8 g (33.5 mmole) of sodium bicarbonate contained in a 500 mL two-necked, round-bottom flask equipped with an addition funnel and drying tube. This mixture is stirred by means of a magnetic stir bar while 14.27 ml (67 mole) of sebacoyl chloride are added dropwise over a 10 minute period. The mixture is continuously stirred for three days at room temperature. The mixture is then washed 5 times with 500 ml of saturated sodium chloride and is then treated carefully with 500 ml of saturated sodium bicarbonate solution. The organic solvent layer is separated and the remaining aqueous layer is washed two times with 100 ml portions of ethyl ether. The pH of the aqueous solution is then adjusted to 1.5 with 6N hydrochloric acid at 0° C. and the mixture is extracted with 200 ml of ethyl acetate. The ethyl acetate extract is dried over anhydrous sodium sulfate, filtered, and the solvent removed with a rotor evaporator. The residue is dissolved in 100 ml of a warm toluene/tetrahydrofuran (3:1 v/v) mixture. After cooling overnight a white precipitate of sebacic acid ester of ricinoleic acid is obtained and removed by filtration. The product is chromatographed on a silica gel column (Aldrich, 230–400 mesh, 1.0×70 cm) with toluene/tetrahydrofuran (3:1 v/v) mixture as eluent. The eluted product is recovered by rotoevaporation of the solvent. Chromatography of this product is performed on a silica gel column (Aldrich, 230–400 mesh, 1.0×70 cm), using a petroleum either (bp 50°–110° C.)/ethyl acetate/acetic acid (80/30/1 v/v/v) mixture as eluent. The product which shows one spot on silica gel TLC plate, $R_f$=0.33 (Baker-flex Silica Gel LB-F, petroleum ether (bp 50°–110° C.)/ethyl acetate/acetic acid (80/30/1 mixture)), is collected as a clear waxy material (mp 70°–72° C.).

The product, which may be called RISE-1, has the following structural configuration:

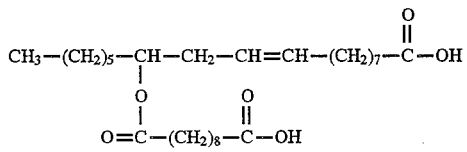

RISE-1 is sebacic acid ester-linked to ricinoleic acid via the 12-OH. RISE-1 inhibits $PLA_2$ activity in vitro and in situ, and inhibits $PLA_2$ induced mouse paw edema. But like pure ricinoleic acid compounds, RISE-1 has no antioxidant activity and does not inhibit rat adjuvant induced arthritis. Limited antioxidant activity is predicted in this structure due to the presence of only a single double bond.

Figure 8:
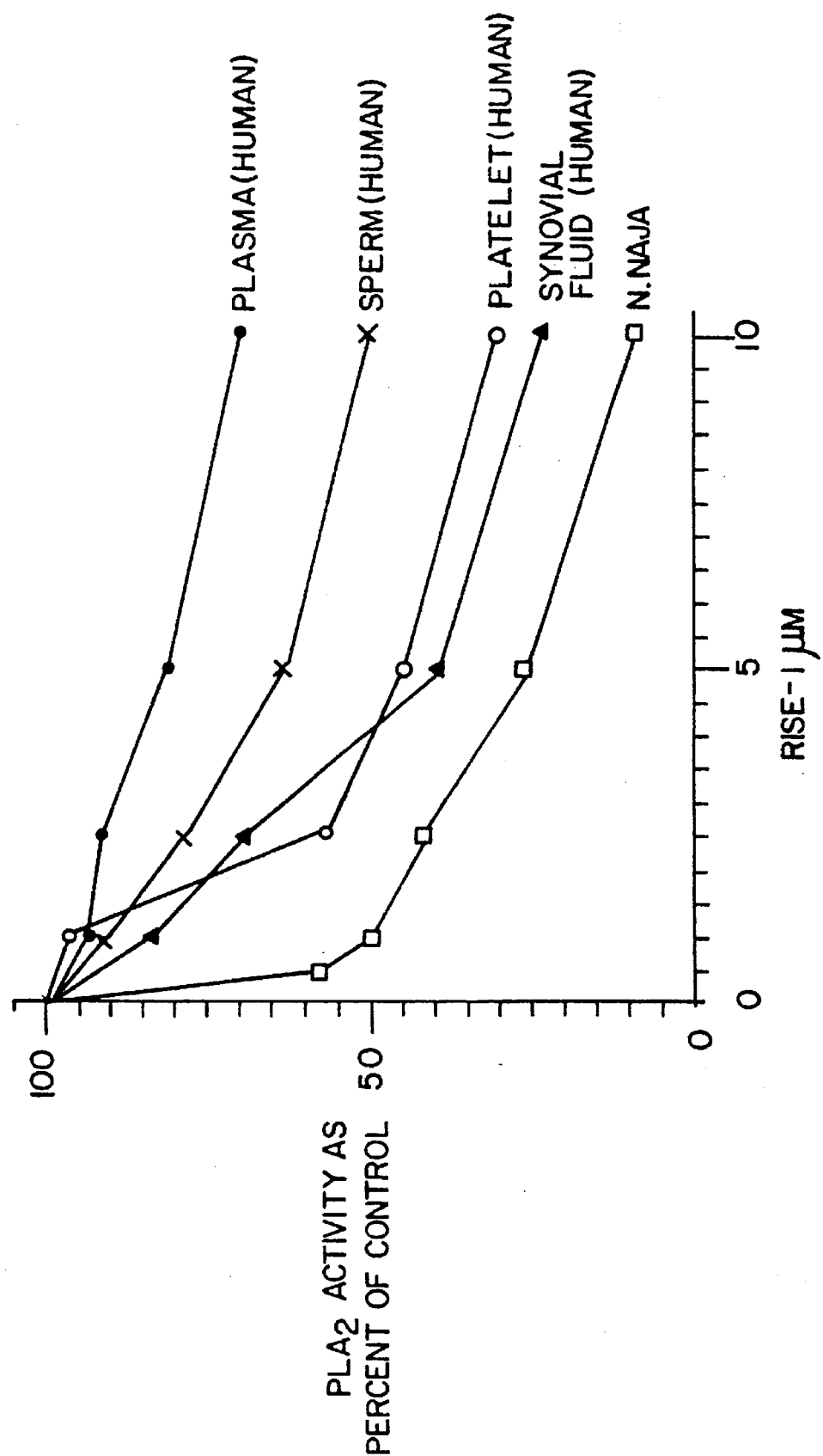
FIG. 8 is a graph illustrating the ability of ricinoleic acid-sebacyl ester polymer to inhibit PLA$_2$ from a variety of sources.

The selective activity of RISE-1 provides a dose related, selective in vitro inhibition of $PLA_2$ derived from plasma, sperm, platelets, human synovial fluid and *N. naja* cobra venom phospholipase. This is illustrated in FIG. 8 of the drawings. Importantly, the wide range of $PLA_2$ enzymes inhibited, i.e., from different sources: human synovial fluid, human plasma, platelets, and sperm suggests that RISE-1 and similar compounds are useful both specifically and non-specifically as inhibitors of this enzyme regardless of enzyme source.

Table 1 set forth below shows the in vivo inhibition by RISE-1 of inflammation induced by the intra-articular injection of human synovial fluid $PLA_2$ ($SF-PLA_2$) into the mouse paw. The mouse paw edema is inhibited in dose related fashion by increasing concentrations of RISE-1 given orally 1.0 hours before induction of the edema by $SF-PLA_2$.

TABLE 1

Inhibition of Human $SF-PLA_2$ Induced Mouse Paw Edema by Oral Administration of RISE-1

|  | % Increase Weight | % Protection |
|---|---|---|
| $PLA_2$ (Control) | 61% | 0% |
| $PLA_2$ + RISE-1 10 mg/kg | 47% | 23% |
| $PLA_2$ + RISE-1 30 mg/kg | 38% | 38% |
| $PLA_2$ + RISE-1 100 mg/kg | 31% | 49% |

Conclusion: RISE-1 has oral anti-inflammatory activity in this model of edema.

Tables 2 and 3 set forth below show the absence of protection provided by RISE-1 against spontaneous oxidation of phosphatidylethanolamine (Table 2) and against arachidonic acid hydroperoxide formation (Table 3).

TABLE 2

Lack of Effect of RISE-1 on the Autooxidation of Phosphatidylethanolamine

| Sample | Time (Hrs) | % Unoxidized PE | % Oxidized PE |
|---|---|---|---|
| PE (control) | 0 | 95.8% | 1.4% |
| PE | 24 | 51.1% | 39.3% |
| PE + RISE-1 25 uM | 24 | 50.6% | 42.0% |
| PE + RISE-1 100 uM | 24 | 49.6% | 42.4% |

TABLE 3

Oxidation of Arachidonic Acid (as Measured by Decreased Turbidity and Hydroperoxide Formation)

| | Turbidity (430 nm) | | Hydroperoxide (nmols) | |
|---|---|---|---|---|
| | Time (hrs) | | | |
| | 0 | 24 | 0 | 24 |
| Control | 1.38 | .387 | 100 | 378 |
| Control + RISE-1 25 uM | 1.33 | .524 | 109 | 437 |
| Control + RISE-1 50 uM | 1.47 | .348 | 109 | 428 |
| Control + BHT 100 uM | 1.31 | 1.283 | 119 | 112 |

BHT = betahydroxytoluene

From the data presented in Tables 2 and 3 it can concluded that RISE-1 has no effect on the autooxidation of arachidonic acid or phosphatidylethanolamine. This contrasts vividly with the effect of other fatty moiety polymers of the invention in this regard and the products of Examples II (RALA), III (RAOA) and IV (OA1RAFA) are shown in Table 4 below to be effective inhibitors for the auto-oxidation of phosphatidylethanolamine.

TABLE 4

Effect of fatty moiety compounds
on the auto-oxidation of phosphatidylethanolamine

| Concentration (μM) | Percent Protection | | |
|---|---|---|---|
|  | RAOA | RALA | OA1RAFA |
| 25 | 16% | 13% | 28% |
| 50 | 16% | 22% | 24% |
| 100 | 13% | 38% | 31% |
| 250 | 22% | 53% | 47% |
| 500 | 27% | 73% | 62% |

Figure 9:
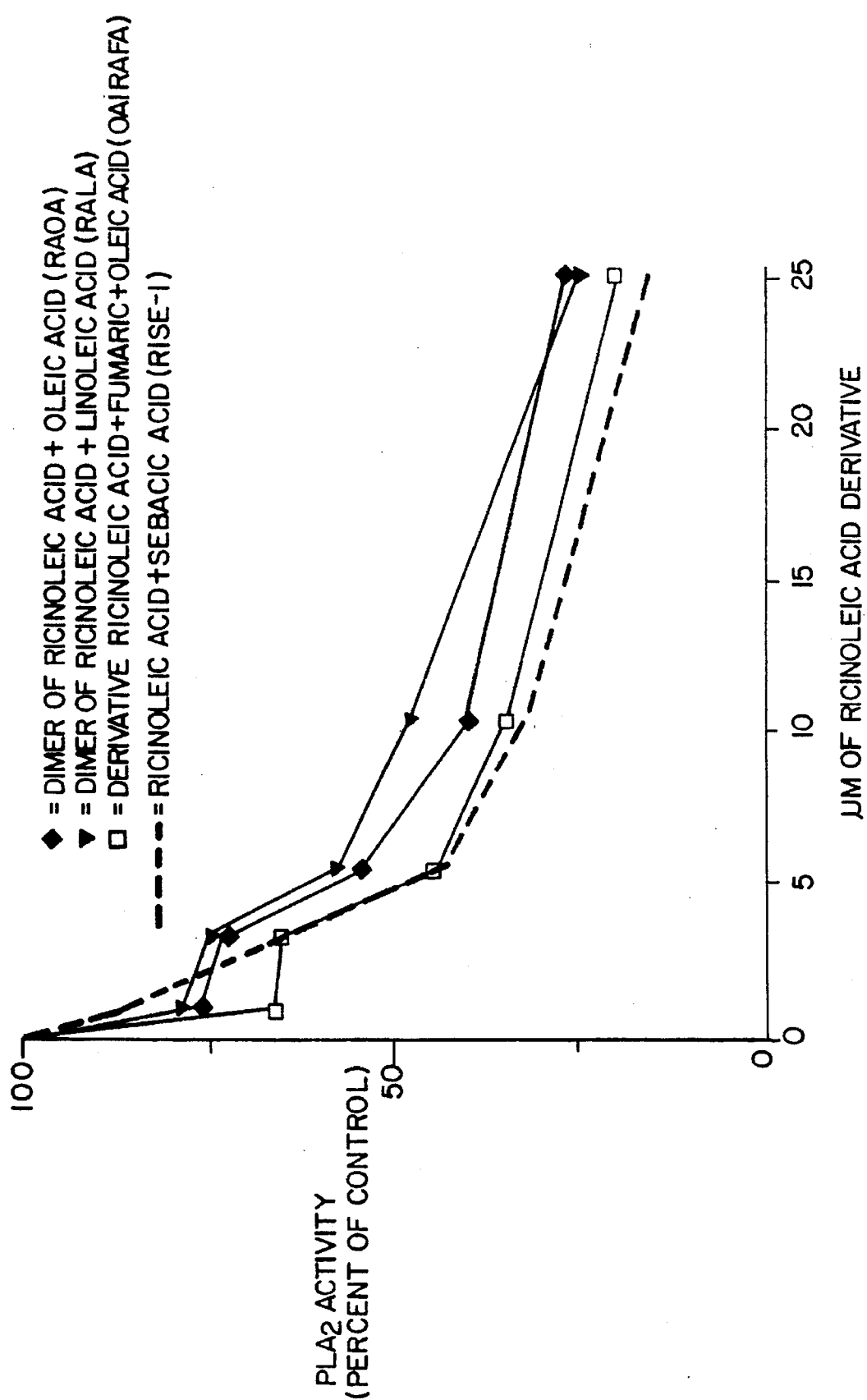
FIG. 9 is a graph illustrating the ability of the compounds of the invention to inhibit PLA$_2$ activity in vitro.

On the other hand, as shown in FIG. 9 of the drawings, RISE-1, RAOA, RALA and OA1RAFA all effectively inhibit human synovial $PLA_2$ activity in a dose-dependent manner where each compound, prepared as a sodium salt, has an $IC_{50}$ of approximately 5 to 10 μM.

The data set forth below in Table 5 illustrates the fact that RISE-1, in a dose related fashion, inhibits arachidonic release from prelabelled human polymorphonuclear leukocytes (PMNs), indicating that RISE-1, despite absence of antioxidant activity, is capable of modulation, i.e., blocking, in dose-related fashion, of the release of arachidonic acid from stimulated white blood cells (PMNs).

TABLE 5

Inhibition of Arachidonic Acid Release from Prelabelled Human PMNs

|  | % Inhibition |
|---|---|
| PMNs alone | 0% |
| PMNs + RISE-1 25 uM | 0% |
| PMNs + RISE-1 50 uM | 19% |
| PMNs + RISE-1 75 uM | 38% |
| PMNs + RISE-1 100 uM | 72% |

Sebacic acid esterified to ricinoleate (RISE-1) lacks anti-oxidant activity, but inhibits $PLA_2$ activity and is anti-inflammatory in the $PLA_2$-induced mouse paw edema model. The lack of anti-oxidant activity is believed to be due to the absence of a cis-double bond in the sebacic acid moiety. But when the esterified moiety is either oleic acid (18 carbons, 1 cis-double bond) or linoleic acid (18 carbons, 2 cis-double bonds) the products now have anti-oxidant activity. And the anti-oxidant activity tends to increase with the number of double bonds (see Table 4 and FIG. 9).

In addition to the foregoing Compounds, many of which comprise derivatives of ricinoleic acids, additional compounds are included within the broad scope of the invention. Some of these compounds are defined structurally by the following generic formula:

$$\begin{array}{c} NH_3^+A \\ | \\ R_1-C-CH_2-O-R \\ | \\ CH_2-O-R \end{array}$$

wherein ⁻A is an organic or inorganic anionic moiety; wherein $R_1$ is —$CH_2$—O—R, a hydrogen molecule or a $C_1$ to $C_4$ aliphatic group; and wherein the R groups may be the same or different and each R group is a fatty moiety.

In this form of the invention the R groups may have one of the following structural formulations:

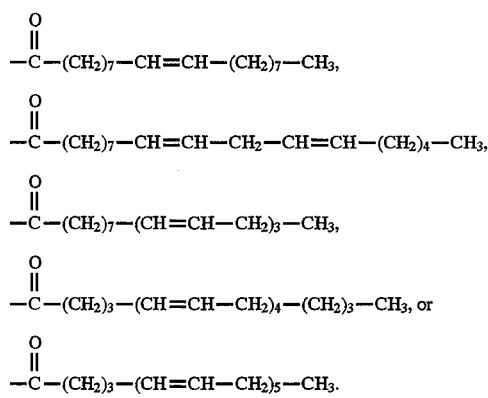

A method for preparing a particularly preferred compound having the foregoing structural configuration is described in Example VI.

EXAMPLE VI

P-Toluene Sulfonate Salt of Tris Trioleate 0.54 g (4.4 mmoles) of tris(hydroxymethyl) aminomethane (Tris, Aldrich), 5.0 g (17.7 mmoles) of oleic acid (Aldrich), and 1.26 g (6.6 mmoles) of p-toluenesulfonic acid monohydrate (Sigma) are mixed in 50 ml of toluene and placed in a 100 ml round-bottomed single-necked flask equipped with a Dean-Stark trap and a Teflon-coated magnetic stirring bar. After bubbling the reaction mixture with $N_2$ gas for 10 minutes, the reaction mixture is heated to reflux. The reaction is continued until a stoichiometric amount of water is recovered (0.38 ml). After removal of a small amount of undissolved material by filtration, the toluene is removed by rotoevaporation to yield a white waxy product. This product is purified on a silica gel column (Aldrich 230–400 mesh, 2.0×55 cm) with 8:2 petroleum ether (bp 60°–90° C.)-ethyl acetate as developing solvent. After eluting with developing solvent the top uncolored layer is carefully removed and the product is extracted with ethyl acetate from the silica gel. The solvent is removed by rotoevaporation and the product is recovered as a p-toluene sulfonic acid salt of tris trioleate having the following structural configuration:

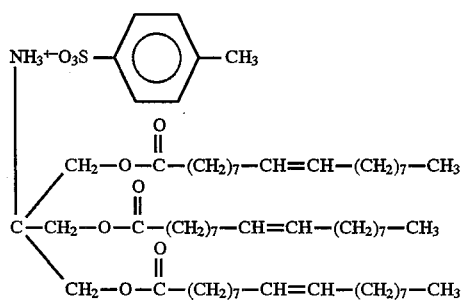

In this procedure, the amine group of the Tris is protected from reacting with the fatty acid because it is in the form of a p-toluene sulfonate salt. Moreover, the p-toluene sulfonic acid acts as a catalyst for the esterification between the alcohol functions on the Tris and the fatty acid.

Another class of compounds within the generic scope of the invention has the following general structural formulation:

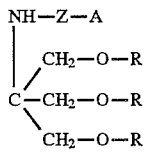

wherein the R groups may be the same or different and each R may be a fatty moiety, wherein Z may be a divalent $C_1$ to $C_5$ aliphatic organic radical, and wherein A may be an organic acid moiety. In this case also the R groups may have structural formulations as set forth in the preceding paragraph. Preferably Z may be $-(CH_2)_n-$ (wherein n is 1 to 5),

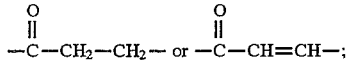

and A may be a carboxyl group or a sulfonyl group. Methods for preparing compounds within this group of compounds are set forth in Examples VII and VIII below.

EXAMPLE VII

TES Trioleate

To a 250 ml single-neck, round-bottom flask is added 1.0 g (4.36 mmoles) of 2-[tris(hydroxylmethyl)-methylamino]-1-ethanesulfonic acid (TES; Aldrich; 99% purity) and 25.0 ml of anhydrous dimethyl formamide (DMF). The flask contents are then cooled to 0° C. in an ice-water bath. 5.25 g (17.45 mmoles) of oleoyl chloride (Aldrich, technical grade) is added dropwise over a 5 minute period. The reaction mixture is stirred at room temperature from 4 days. The DMF is removed by distillation at 40°–45° C. under reduced pressure. The residue is a viscous oil which is transferred to a flask containing 200 ml acetone and vigorously stirred until a slightly cloudy solution is formed. This solution is refrigerated overnight. The precipitate formed is collected by filtration and washed with distilled acetone (20 ml) five times. The product is dried in vacuo at room temperature for 24 h (2.32 g, 52%) and has the following structural configuration:

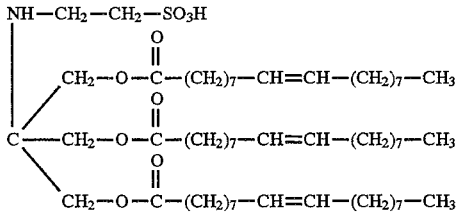

EXAMPLE VIII

Tris Trioleate Maleic Acid Amide 2.0 g (1.96 mmoles) of tris trioleate is dissolved in 10 ml of anhydrous $CH_2Cl_2$ in a 50 ml single-neck round-bottom flask. The solution is cooled to 0° C. in an ice-water bath and 0.42 g (1.96 mmoles) of $CH_3ONa$ (Aldrich, 25% by weight in $CH_3OH$) is added dropwise under vigorous stirring. After 30 minutes the solvents are removed by rotoevaporation and the residue dried in vacuo at room temperature for 24 hours. To this material, 10 ml of freshly distilled $CH_2Cl_2$ and 0.37 g (3.90 mmoles) of recrystallized maleic anhydride is added. The reaction mixture is stirred at room temperature for 24 hours. The methylene chloride is removed by rotoevaporation and the viscous oil obtained is transferred to a 250 ml beaker containing 100 ml acetone and 5 ml of $H_2O$. This is vigorously stirred until a clear solution forms. The solution is refrigerated overnight and until a viscous material forms at the bottom of the beaker. The upper layer is recovered and the acetone rotoevaporated. The residue is stirred with 10 ml $CHCl_3$ for 15 minutes and the insoluble material is removed by filtration. The $CHCl_3$ is removed by rotoevaporation and the residual oil is then similarly treated with benzene to further remove impurities. The final product is a waxy-like material (0.82 gm 37%) having the following structural configuration:

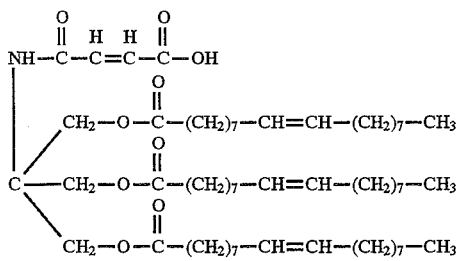

Yet another group of compounds within the generic scope of the invention may be described by the following generic structural configuration

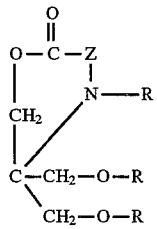

wherein the R groups may be the same or different and each is a fatty moiety and Z is a $C_1$ to $C_5$ aliphatic organic radical. In this form of the invention the R groups may be

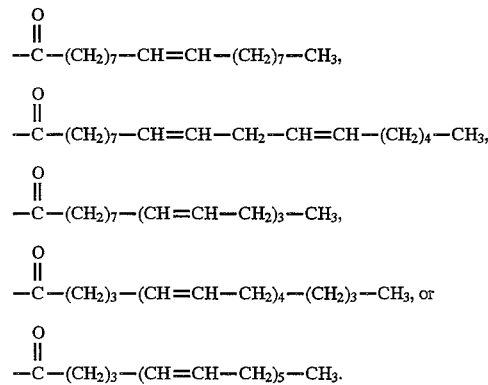

A method for preparing a compound within this group of compounds is set forth in Example IX below.

EXAMPLE IX

Tricinyl Trioleate 0.67 g (3.75 mmoles) of N-[tris(hydroxymethyl)methyl] glycine (Tricine; Aldrich) is suspended in 15 ml of anhydrous DMF and placed in a 100 ml round-bottom single-necked flask equipped with a Teflon-coated magnetic stirring bar. The suspension is cooled to 0° C. in an ice-water bath, and 5.6 g (18.75 mmoles) of oleoyl chloride is added dropwise. A solution containing 15 ml of anhydrous $CH_2Cl_2$ and 2.7 g (22.5 mmoles) of 4-dimethylaminopyridine is added to the reaction mixture and the resultant admixture is warmed to room temperature, and stirred for 22 hours. The admixture is filtered and the solvents are removed under reduced pressure. 200 ml of ethyl acetate is added to the residue and insoluble material is removed by filtration. The filtrate is washed with 100 ml portions of 5% $NaHCO_3$ aqueous solution (saturated with NaCl) three times. The ethyl acetate layer is dried over magnesium sulfate, and then the ethyl acetate is rotoevaporation to yield a crude product which is then purified by chromatography using a silica gel column (Aldrich, 230–400 mesh, 2.0×55 cm) and 8:2 petroleum ether (bp 60°–90° C.)-ethyl acetate as developing solvent. The fractions containing the product are combined and the solvent is evaporated. The product, which may be referred to as an amide-diester lactone, shows only one spot on TLC, $R_f$ 0.44 (Aldrich pre-coated silica gel LC sheet: 8:2 petroleum ether-ethyl acetate) and has the following structural configuration:

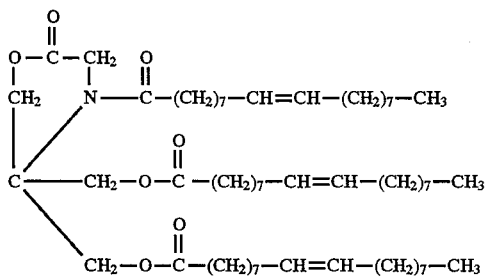

If the foregoing product is contacted with NaOH during sample preparation, the ring opens to present an amide diester hydroxy acid compound having the following structural configuration:

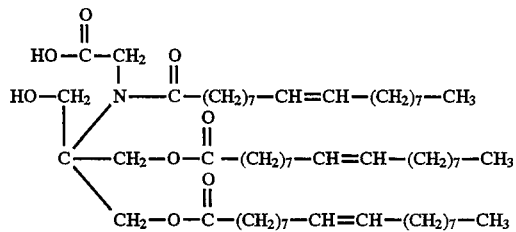

Still another group of compounds which embody the concepts and principles of the invention may be described by the general formula:

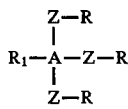

wherein A is a $C_1$–$C_7$ aliphatic group, $R_1$ may be —Z—R, a $C_1$–$C_4$ alkyl group, a nitro group, an amino group, a carboxylic acid group, a sulfonic acid group, or a hydrogen atom, the Z groups, which may be the same or different, may be —O— or —NH—, and the R groups, which also may be the same or different, may be fatty moieties as described above.

Other compounds in the foregoing class of compounds may be represented by the following subgeneric structural formulas:

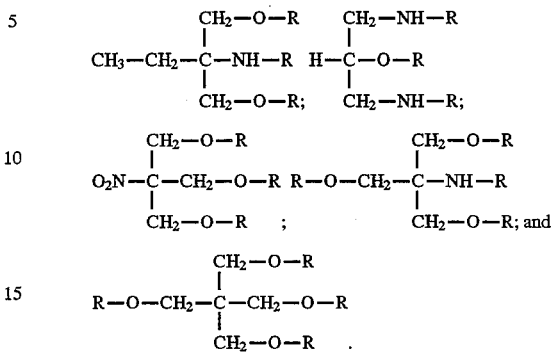

As can be appreciated, the compounds in this class may be prepared from multivalent hydroxides and amides by esterification and/or amidification using an appropriate fatty acid compound. Suitable starting materials include 2-amino-2-hydroxymethyl-1-hydroxybutane; 1,3-diamino-2-hydroxypropane; 1,3 dihydroxy-2-amino-2-hydroxymethylpropane; and 1,3 dihydroxy-2,2-dihydroxymethylpropane. One shortcoming of the compounds of this class is their relative lack of solubility in water. However, suitable dose forms may be prepared utilizing DMSO as a solvent.

A procedure for preparing a specific compound in this class is set forth in Example X.

EXAMPLE X 1,3-Diamino-2-hydroxypropane Oleoyl Diamide Ester

In a 1 liter reaction flask, 20 g (0.22 mole) of 1,3 diamino-2-hydroxypropane are dissolved in 500 ml of $CH_2Cl_2$ containing 88.1 g (0.72 mole) dimethylaminopyridine. The solution is cooled in an ice bath while 213.6 g (0.71 mole) of oleoyl chloride (70%, Aldrich) is added with stirring over a 2 hour period. The reaction mixture is then stirred at room temperature for 70 hour. The precipitated salts are removed by filtration and the solvent is removed by rotoevaporation. The residual oil is dissolved in 600 ml of ethyl acetate and the insoluble material is removed by filtration. The ethyl acetate is washed with a saturated $NaCl/H_2O$ solution (3 times). The non-aqueous solution is dried over anhydrous $MgSO_4$, filtered, and the solvent removed by rotoevaporation. The oil obtained is washed with 250 ml of methanol (4 times). The residue is taken up in 800 ml of ethyl acetate treated with 15 g of charcoal and filtered. The solution is passed through a silica gel column (3.0×10 cm) and the recovered solution is concentrated to yield a viscous light yellow oil (141.6 g). TLC gave one spot and the structure is verified by IR, H and $^{13}C$ NMR. The structural configuration is as follows:

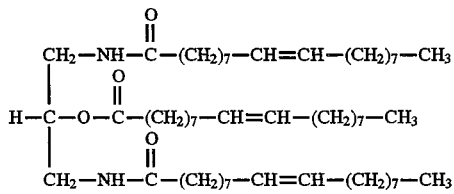

The relative abilities of some of the compounds described above to perform as anti-oxidants and as anti-$PLA_2$ agents is illustrated below in TABLE 6 wherein the polymers compared are as follows:

| | |
|---|---|
| PX-1 | (PGB$_x$) |
| PX-2 | (ricinoleate/fumarate monomer) |
| PX-3 | (EXAMPLE III dimer) |
| PX-4 | (EXAMPLE II dimer) |
| PX-5 | (EXAMPLE IV dimer) |
| PX-6 | (ricinoleate/ricinoleate dimer) |
| PX-7 | (EXAMPLE I dimer) |
| PX-8 | (ricinoleate/oleate/maleate dimer) |
| PX-9 | (tartrate/linoleate/linoleate dimer) |
| PX-10 | (tartrate/oleate/oleate dimer) |
| PX-11 | (EXAMPLE IX trimer) |
| PX-12 | (EXAMPLE VI trimer) |
| PX-13 | (EXAMPLE VII trimer) |
| PX-14 | (tris trilinoleate trimer) |
| PX-15 | (tricine trilinoleate trimer) |

The terms monomer, dimer and trimer in the foregoing list and as used throughout the present description define the number of $C_{16}$ to $C_{20}$ fatty moieties present in the particular molecule. That is to say, a monomer has one such fatty moiety, a dimer has two, a trimer has three, etc.

TABLE 6

Comparative Table: Fatty Moiety Polymers (PX)

| Compound Compound | IC-50 Anti-Oxidant Activity | IC-50 Anti-PLA$_2$ Activity |
|---|---|---|
| PX-1 | 40 uM | 1–5 uM |
| PX-2 | >500 uM | nd* |
| PX-3 | >500 uM | 7.2 uM |
| PX-4 | 210 uM | 10.0 uM |
| PX-5 | 300 uM | 5.0 uM |
| PX-6 | 300 uM | 4.5 uM |
| PX-7 | 130 uM | 7.0 uM |
| PX-8 | 140 uM | 3.5 uM |
| PX-9 | 100 uM | 7.5 uM |
| PX-10 | 60 uM | 7.0 uM |
| PX-11 | 145 uM | 2.6 uM |
| PX-12 | 50 uM | 1.5 uM |
| PX-13 | 60 uM | 2.2 uM** |
| PX-14 | 70 uM | 4.4 uM |
| PX-15 | nd* | 19.2 uM |

*nd = not detectable at ≦ 500 uM
**most effective vs PLA$_2$-induced mouse paw edema; administered single dose orally: IC50 approx 15 mg/kg The polymers (dimers, trimers, tetramers, etc.) of cis-unsaturated fatty acids and the other compounds having at least two cis-unsaturated straight chain fatty radicals, as described above, affect fundamental membrane phospholipid reactions of phospholipase-induced degradation and free radical peroxidation. The discovery of these dual properties, anti-phospholipase and anti-oxidant activities of these compounds establishes a sound scientific basis for the molecular action thereof in protecting the cell and its membrane from injury. The data set forth above confirms, with experimental results, that these compounds are potent anti-inflammatory and cytoprotective agents.

The appropriate dosage of the cis-unsaturated fatty moiety compounds of the invention for treatment of mammals, including humans, against phospholipase mediated injure and/or inflammation should be in the range of from about 10 to about 100 mg per kg (mg/kg) of body weight when the compound is administered orally or intraperitoneally (IP). When administered intravenously, the dosage should be approximately 50% of the oral or IP dosage to achieve the same level of the drug in the blood stream. In this regard, it should be noted that a lethal dose may be in the range of about 100 to about 400 mg/kg in small mammals and the administered dose should thus be well below that level. The described dosage should also be appropriate for prevention of human platelet aggregation or blood thinning. As is known to those skilled in the art, therapeutic doses expressed in terms of amounts per kilogram of body weight or surface area may be extrapolated from mammal to mammal, including to human beings.

The compounds of the present invention are particularly useful when applied topically to a wound. In this regard, the compounds may be incorporated into conventional ointment, lotion or aerosol formulations. Ointments may be prepared by incorporating 0.1 to 10% of the compound as an oil or sodium salt into an ointment base containing emulsifying agents such as stearic acid, triethanolamine and/or cetyl alcohol. the formulation may also include ingredients such as glycerol, water and preservatives as required.

Water based lotions may contain the compounds of the invention as an oil or as a sodium salt in amounts ranging from 0.1 to 5.0% by volume. Such lotions may contain glycerins and/or bentonite as suspending agents as is well known in the art.

The compounds may also be incorporated into classical (one or two phase) or non-classical (aqueous emulsion) aerosol formulations. Such formulations include the compounds and an appropriate propellant carrier in which the compounds are dissolved or dispensed. In the classical form the active ingredients are generally used as an oil dispersion or in solution in an organic solvent such as ethanol. In the non-classical form the active ingredient is dissolved in water. In each case the concentration of the active ingredient in the carrier may be about 0.1 to 10% by weight or volume.

The compounds of the invention may also be highly useful in the form of gauze bandages which have been coated or impregnated with a solution or dispersion of the active material.

Of particular advantage is the fact that the cis-unsaturated straight chain fatty moiety compounds described above function pharmacologically at the site of inhibitory action for the arachidonate cascade, and preferentially effect stimulus-induced mobilization of arachidonate. Inhibition of PLA$_2$ depresses the production of both prostaglandins and leukotrienes in stimulated or inflamed cells. Importantly, the polymers described above have a much more pronounced effect on stimulus-induced, than on controlled release of arachidonate indicating a selective effect on the former. Moreover, when phospholipids are peroxidized, the polymer compounds described above are capable of inhibiting the degradation of such lipids by lysosomal phospholipase C, indicating that these compounds can protect already damaged (oxidized) membranes.

Thus, multiple actions are responsible for the anti-inflammatory activity of the fatty moiety compounds of the invention, and on the basis of inflammatory models, it is evident that these compounds can effectively rival or replace both currently available steroids and NSAIAs in the treatment of inflammation, making the polymerized cis-unsaturated straight chain fatty moiety compounds of the invention candidates for clinical application and usefulness in localized and systemic injury and disease.

The fact that production of the prostaglandin, thromboxane, from free arachidonic acid is required for platelet function indicates that the unsaturated fatty moiety polymers described above should affect the platelet aggregation release reaction.

PLA$_2$ is present at widely different levels in a variety of human cells and fluids tested. Inflammation is associated with a significant rise in extracellular phospholipases, and the polymers of cis-unsaturated fatty moieties described above have the ability to inhibit these enzymes.

Phospholipases are released from pathogenic invading organisms and the polymers described above act by inhibiting the action of these membrane-destructive enzymes produced by pathogens of bacterial, protozoal, viral, Rickettsial, helminthic and fungal origin. The action of the compounds of the invention in preventing inflammation or tissue injury is manifested by inhibition of PLA$_2$ at its source from infecting organisms or inhibition by blocking host responses to infection or injury.

In addition, there is evidence that tumor metastases or invasion is associated with endogenous activity on the part of malignant cells and the expression of phospholipases and their inhibition can play a role in the control of differentiation and functional integrity as well as the processes of carcinogenesis and aging. In the latter case, the polymers of unsaturated fatty moieties described above prolong life in animal models and minimize membrane alterations in living organisms produced by carcinogens (mutagens) and photo-oxidizers which are radiation-like in their cell damaging activity.

The polymers of unsaturated fatty moieties described above, by protecting lipid membranes and possessing anti-oxidant activity, are potent anti-oxidants for preservation, not only of living cells and tissues, but their action makes them effective as a preservatives of food, tissue and chemical agents subject to oxidative injury. For purposes of protecting and preserving food subject to oxidation injury, the fatty moiety compounds of the invention may be used at concentrations of approximately 0.1 to 100 µM. These molarities are calculated as the molarity that would be obtained if the drug were dissolved in a weight of water which is the same as the weight of the food stuff to be preserved. For example, in vitro, anti-oxidant and/or anti-phospholipase applications, concentrations of from about 0.1 to about 500 µM should be effective.

The essence of the action of the polymers of cis-unsaturated straight chain fatty moieties described above is the role they play in resisting injury and permitting repair to phospholipid/protein membranes. They also play a protective role in the stabilization of proteins. These compounds clearly are cytoprotective agents which protect the cell membrane from toxic, pathogenic, or age mediated events in the cellular or supportive environment. In final analysis, the minimal dose of the Unsaturated fatty moiety compounds of the invention depends upon empirical considerations for relief from phospholipase mediated injury and/or inflammation or to accomplish the desired cytoprotective function. The maximum dose depends principally on the necessity of avoidance of undesired side-effects and lethal doses.

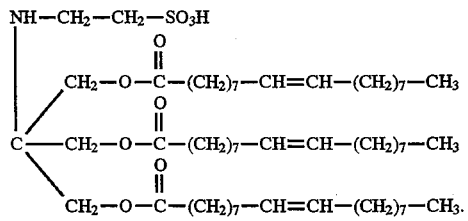

We claim:

1. A compound having the formula

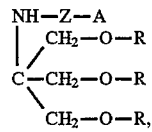

wherein each R is a fatty moiety having from sixteen to twenty carbon atoms and at least one cis-unsaturated double bond, Z is a C$_1$ to C$_5$ aliphatic organic radical and A is an organic acid moiety.

2. A compound as set forth in claim 1, wherein said R groups are the same or different and each is

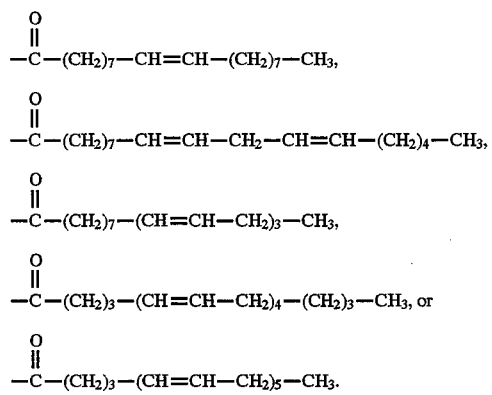

3. A compound as set forth in claim 2, wherein Z is —(CH$_2$)$_n$—, and n is 1 to 5.

4. A compound as set forth in claim 3, wherein n is 2 and A is a sulfonyl group.

5. The compound of claim 1 having the formula